United States Patent
Kato et al.

(10) Patent No.: US 10,178,977 B2
(45) Date of Patent: Jan. 15, 2019

(54) X-RAY DIAGNOSTIC APPARATUS AND IMAGE PROCESSING APPARATUS

(71) Applicant: Toshiba Medical Systems Corporation, Otawara-shi (JP)

(72) Inventors: Hisanori Kato, Otawara (JP); Yasuhiro Sugawara, Nasushiobara (JP); Yoshimasa Kobayashi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/695,289

(22) Filed: Apr. 24, 2015

(65) Prior Publication Data

US 2015/0317771 A1 Nov. 5, 2015

(30) Foreign Application Priority Data

Apr. 30, 2014 (JP) .................... 2014-094203

(51) Int. Cl.
*G06K 9/00* (2006.01)
*A61B 6/00* (2006.01)
(Continued)

(52) U.S. Cl.
CPC .......... *A61B 6/4291* (2013.01); *A61B 6/4233* (2013.01); *A61B 6/5205* (2013.01);
(Continued)

(58) Field of Classification Search
None
See application file for complete search history.

(56) References Cited

U.S. PATENT DOCUMENTS 5,878,108 A * 3/1999 Baba .................... A61B 6/5282
378/7
7,492,947 B2 2/2009 Nanbu
(Continued)

FOREIGN PATENT DOCUMENTS

| CN | 103491875 A | 1/2014 |
|---|---|---|
| JP | 05-244508 | 9/1993 |
| JP | 3683914 | 8/2005 |

OTHER PUBLICATIONS

Combined Chinese Office Action and Search dated May 31, 2017 in Patent Application No. 201510209927.0 (with English language translation of categories of cited documents).

*Primary Examiner* — Sean M Conner
(74) *Attorney, Agent, or Firm* — Oblon, McClelland, Maier & Neustadt, L.L.P.

(57) ABSTRACT

According to an embodiment, a grid is provided between an X-ray generator and a flat panel detector. Processing circuitry configured to convert original image based on X-rays having passed through the grid and detected into a plurality of pieces of frequency band data, remove interference fringes contained in at least one piece of frequency band data among the pieces of frequency band data, reduce noise contained in the pieces of frequency band data, correct a scattered radiation of the original image based on a scattered radiation contained in the X-rays having passed through the grid and a scattered radiation contained in X-rays having passed through a grid that removes scattered radiation to a larger extent than the grid, and synthesize a plurality of pieces of frequency band data to generate image.

19 Claims, 14 Drawing Sheets

(51) Int. Cl.
*G06T 5/00* (2006.01)
*G06T 5/10* (2006.01)

(52) U.S. Cl.
CPC .......... *A61B 6/5258* (2013.01); *A61B 6/5282* (2013.01); *G06T 5/002* (2013.01); *G06T 5/10* (2013.01); *G06T 2207/10116* (2013.01)

(56) References Cited

U.S. PATENT DOCUMENTS

| | | | | |
|---|---|---|---|---|
| 2008/0080663 | A1* | 4/2008 | Haerer | G06T 5/002 378/7 |
| 2008/0175350 | A1* | 7/2008 | MacDonald | G01N 23/20 378/37 |
| 2010/0272236 | A1* | 10/2010 | Hirooka | A61B 6/06 378/62 |
| 2012/0099705 | A1* | 4/2012 | Murakoshi | A61B 6/4291 378/85 |
| 2013/0142308 | A1* | 6/2013 | Ishii | G01N 23/04 378/62 |
| 2014/0086472 | A1* | 3/2014 | Hasegawa | G06T 5/002 382/132 |
| 2014/0126690 | A1* | 5/2014 | Yamaguchi | A61B 6/484 378/36 |
| 2016/0354051 | A1* | 12/2016 | Enomoto | A61B 6/4241 |

* cited by examiner fn: NYQUIST FREQUENCY

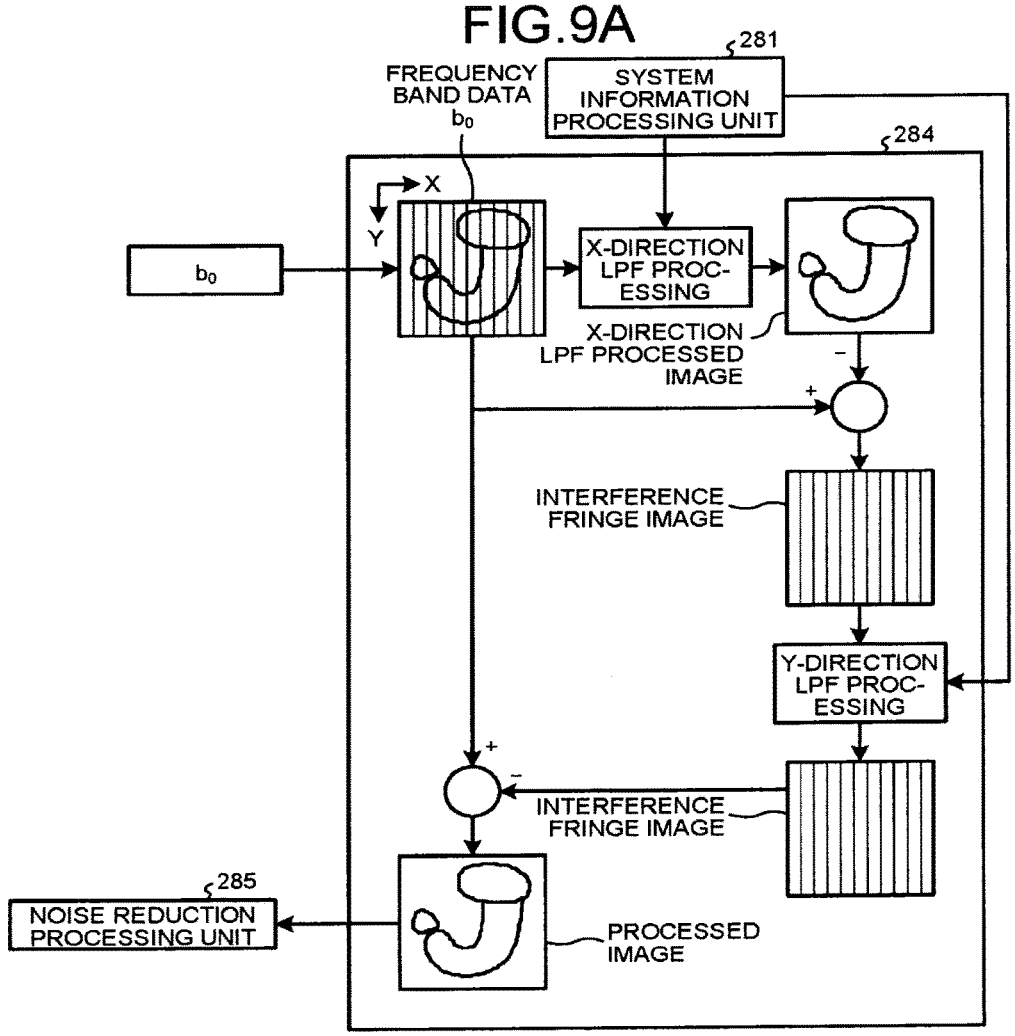
FIG.9A
FIG.9B
FREQUENCY CHARACTERISTIC OF ONE-DIMENSIONAL SPATIAL FILTER (LPF)
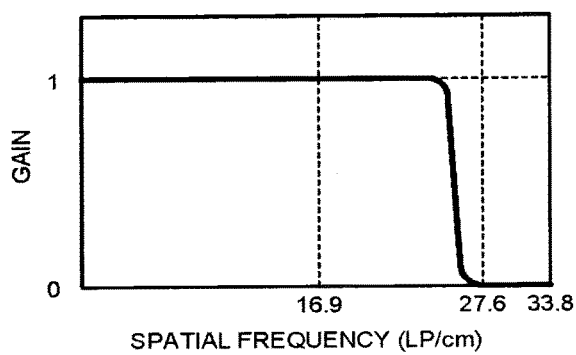

X-RAY DIAGNOSTIC APPARATUS AND IMAGE PROCESSING APPARATUS

CROSS-REFERENCE TO RELATED APPLICATION(S)

This application is based upon and claims the benefit of priority from Japanese Patent Application No. 2014-94203, filed on Apr. 30, 2014, the entire contents of all of which are incorporated herein by reference.

FIELD

Embodiments described herein relate generally to an X-ray diagnostic apparatus and an image processing apparatus.

BACKGROUND

Conventional X-ray diagnostic apparatuses include a grid on the detection face side of an X-ray detector in order to remove scattered X-rays (scattered radiation) occurring in a subject. The grid, for example, has lead foils that absorb X-rays and intermediate substances (aluminum or fiber, for example) that absorb less X-rays alternately and causes the lead foils to absorb the scattered radiation to remove the scattered radiation. The grid has the lead foils and the intermediate substances so as to give a certain lattice density (the number of lead foils per unit length).

When a flat panel detector (FPD) is used as the X-ray detector in the X-ray diagnostic apparatus, interference fringes caused by pixels of the FPD and a lattice of the grid may occur in X-ray images. Such interference fringes as artifacts deteriorate the performance of diagnosing X-ray images. In view of this, some methods are known as methods for inhibiting the occurrence of such interference fringes. Examples thereof include matching the lattice density of the grid with the pixel pitch of the FPD and using a grid having a lattice density high enough not to be able to convert input signals even by the FPD. However, there may be cases where the above conventional techniques have difficulty in reducing radiation exposure while maintaining image quality.

BRIEF DESCRIPTION OF THE DRAWINGS

FIG. 9A is a diagram for illustrating interference fringe removal processing by an interference fringe removal processing unit according to the first embodiment;

FIG. 9B is a diagram for illustrating the interference fringe removal processing by the interference fringe removal processing unit according to the first embodiment;

DETAILED DESCRIPTION

According to an embodiment, an X-ray diagnostic apparatus comprising, an X-ray generator, a flat panel detector, a grid and processing circuitry. The X-ray generator configured to generate X-rays. The flat panel detector configured to detect the X-rays. The grid provided between the X-ray generator and the flat panel detector. The processing circuitry configured to convert original image data based on X-rays having passed through the grid and detected by the flat panel detector into a plurality of pieces of frequency band data. The processing circuitry configured to remove interference fringes contained in at least one piece of frequency band data among the pieces of frequency band data. The processing circuitry configured to reduce noise contained in the pieces of frequency band data. The processing circuitry configured to correct a scattered radiation component of the original image data based on a scattered radiation component contained in the X-rays having passed through the grid and a scattered radiation component contained in X-rays having passed through a grid that removes scattered radiation to a larger extent than the grid. The processing circuitry configured to synthesize a plurality of pieces of frequency band data after being processed by the respective processing units to generate image data.

The following describes embodiments of an X-ray diagnostic apparatus and an image processing apparatus in detail with reference to the drawings. The following describes an X-ray image diagnostic system including the X-ray diagnostic apparatus according to the present application as an example. The following describes an X-ray diagnostic apparatus that performs examination and treatment on alimentary canals, the urinary organs, orthopedics, interventional radiology (IVR), or the like as the X-ray diagnostic apparatus according to the present application as an example. Embodiments according to the present application are not so limited.

First Embodiment

Figure 1:
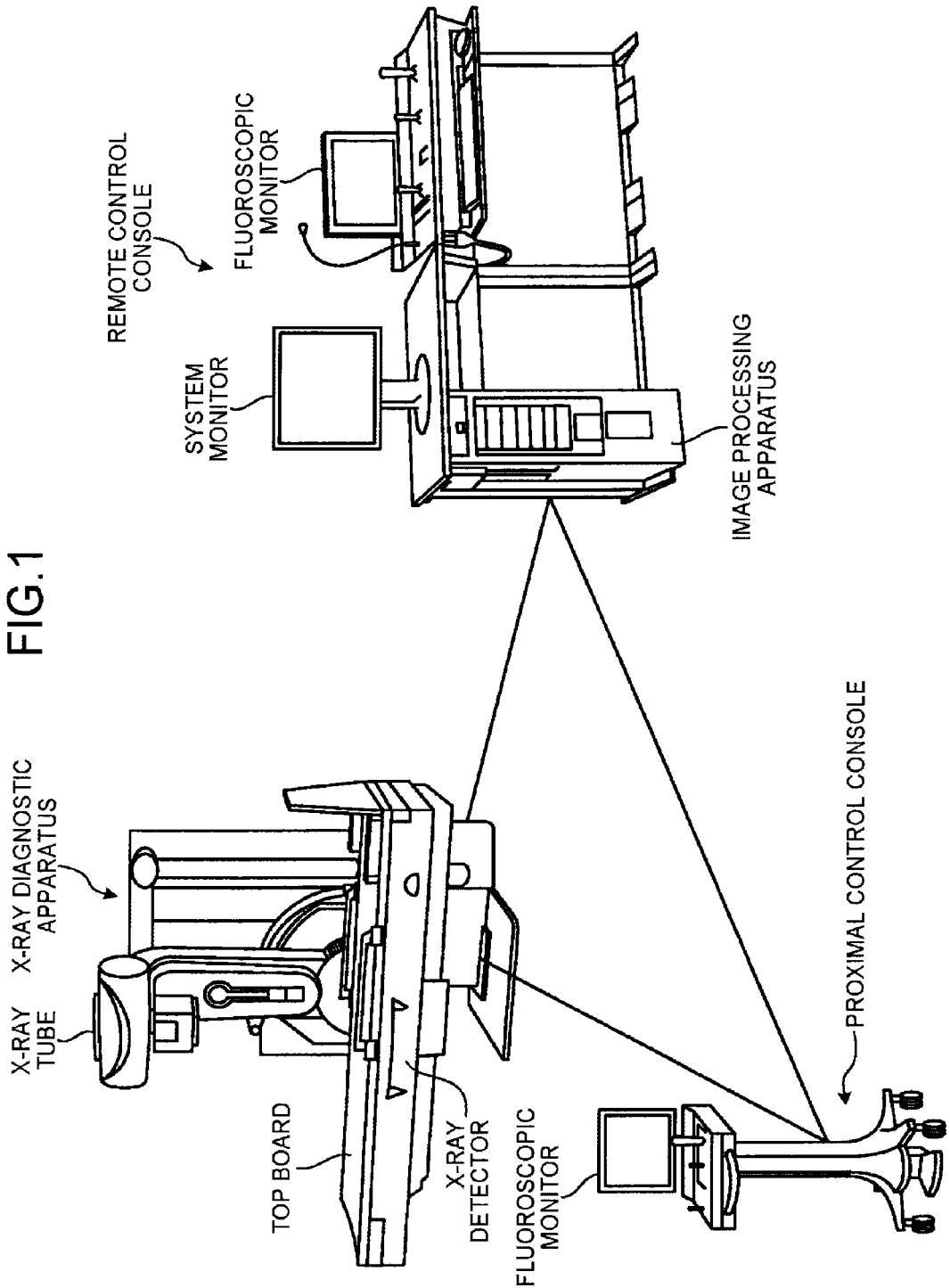
FIG. 1 is a diagram for illustrating an example of an X-ray image diagnostic system according to a first embodiment.

First, an example of an X-ray image diagnostic system according to a first embodiment will be described with reference to FIG. 1. FIG. 1 is a diagram for illustrating an example of the X-ray image diagnostic system according to the first embodiment. As illustrated in FIG. 1, for example, in the X-ray image diagnostic system according to the first embodiment, an X-ray diagnostic apparatus main body including an X-ray tube, a top board, and an X-ray detector, a proximal control console including a fluoroscopic monitor, and a remote control console including an image processing apparatus, a system monitor, and a fluoroscopic monitor are connected to each other. An operator in an operation room, for example, operates the remote control console, thereby causing the apparatus main body to perform operations such as tilting the top board mounting a patient (subject) and moving an imaging system including the X-ray tube and an X-ray movable diaphragm upward and downward and to at the same time perform fluoroscopy and photography. The operator observes fluoroscopic images displayed on the fluoroscopic monitor provided in the remote control console or photographed images and fluoroscopic images displayed on the system monitor. An operator in an examination room, for example, causes the apparatus main body to perform similar processing to the above processing by operating the proximal control console and observes various images displayed on the fluoroscopic monitor provided in the proximal control console or an examination room monitor.

Figure 2:
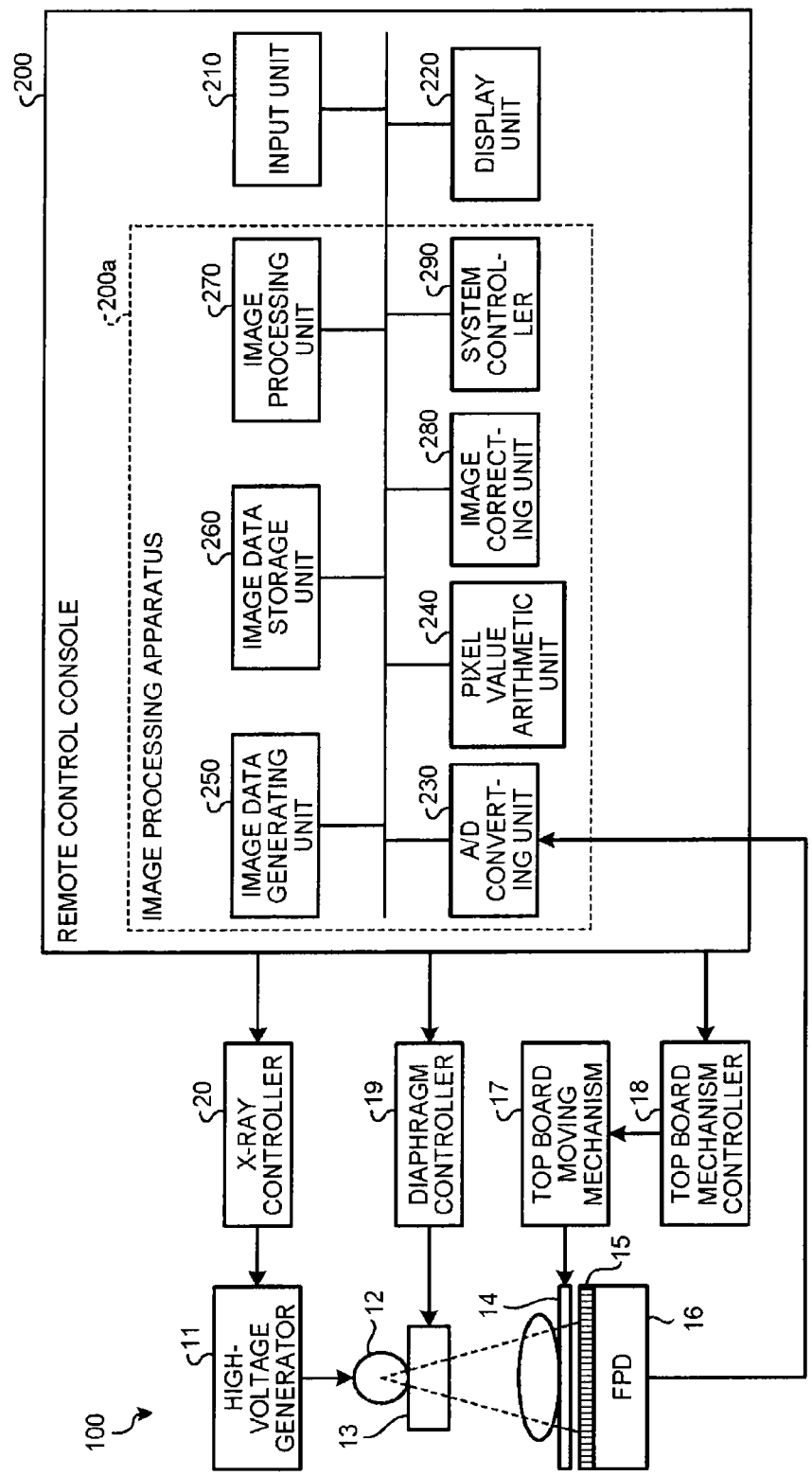
FIG. 2 is a diagram illustrating an example of the configuration of an X-ray image diagnostic apparatus according to the first embodiment.

Next, an example of the configuration of the X-ray diagnostic apparatus according to the first embodiment will be described. FIG. 2 is a diagram illustrating an example of the configuration of an X-ray diagnostic apparatus 1 according to the first embodiment. As illustrated in FIG. 2, for example, the X-ray diagnostic apparatus 1 includes an apparatus main body 100 and a remote control console 200. As illustrated in FIG. 2, the apparatus main body 100 includes a high-voltage generator 11, an X-ray tube 12, an X-ray movable diaphragm 13, a top board 14, a grid 15, a flat panel detector (FPD) 16, a top board moving mechanism 17, a top board mechanism controller 18, a diaphragm controller 19, and an X-ray controller 20 and is placed in the examination room. As illustrated in FIG. 2, the remote control console 200 includes an image processing apparatus 200a, an input unit 210, and a display unit 220 and is placed in the operation room, for example.

Although not illustrated, an injector for injecting a contrast medium through a catheter inserted into the subject may be connected to the X-ray diagnostic apparatus 1. Although not illustrated, a proximal control console includes a fluoroscopic monitor, displays images generated by the X-ray diagnostic apparatus 1, and accepts various operations for operating the X-ray diagnostic apparatus 1. Specifically, the proximal control console is connected to the X-ray diagnostic apparatus 1 via wired or wireless communication and transmits information on operations through an input unit to the X-ray diagnostic apparatus 1, thereby causing a system controller 290 of the remote control console 200 to perform various pieces of control.

The high-voltage generator 11 generates a high voltage under the control of the X-ray controller 20 and supplies the generated high voltage to the X-ray tube 12. The X-ray tube 12 generates X-rays using the high voltage supplied from the high-voltage generator 11.

The X-ray movable diaphragm 13 narrows the X-rays generated by the X-ray tube 12 so as to be selectively applied to a region of interest of the subject under the control of the diaphragm controller 19. The X-ray movable diaphragm 13 has slidable four diaphragm blades, for example. The X-ray movable diaphragm 13 slides these diaphragm blades under the control of the diaphragm controller 19, thereby narrowing and applying the X-rays generated by the X-ray tube 12 to the subject. The top board 14 is a bed for mounting the subject and is arranged on a berth not illustrated.

The grid 15 is arranged between the top board 14 and the FPD 16 to remove part of scattered radiation contained in the X-rays having passed through the subject. The grid 15, for example, has lead foils that absorb X-rays and intermediate substances that absorb less X-rays alternately. The grid 15 is a focusing grid in which the lead foils are inclined toward a point on a central line of the grid in a direction vertical to the grid face or a parallel grid in which the lead foils are arranged in parallel to each other. The FPD 16 detects the X-rays having passed through the grid 15. The FPD 16 has detection elements arranged in a matrix, for example. The respective detection elements convert the X-rays having passed through the grid 15 into electric signals, accumulate them, and transmit the accumulated electric signals to an analog (A)/digital (D) converting unit 230 of the remote control console 200.

The top board moving mechanism 17 is a mechanism for moving or tilting the top board 14 under the control of the top board mechanism controller 18. The top board mechanism controller 18 controls the top board moving mechanism 17 under the control of the system controller 290 of the remote control console 200 described below, thereby adjusting the movement and tilting of the top board 14. The diaphragm controller 19 adjusts the opening of the diaphragm blades of the X-ray movable diaphragm 13 under the control of the system controller 290 of the remote control console 200 described below, thereby controlling the irradiation range of the X-rays applied to the subject.

The X-ray controller 20 causes the high-voltage generator 11 to generate a high voltage and to supply the generated high voltage to the X-ray tube 12 under the control of the system controller 290 of the remote control console 200 described below. The X-ray controller 20, for example, controls an application voltage, application time, application timing, and the like of the high-voltage generator 11 based on X-ray irradiation conditions supplied from the system controller 290 and pixel value information supplied from a pixel value arithmetic unit 240 described below, thereby controlling a tube current, tube voltage, X-ray irradiation time, X-ray irradiation timing, pulse width, and the like of the X-ray tube 12.

The input unit 210 is placed in the operation room and accepts various instructions from an operator who operates the X-ray diagnostic apparatus 1. The input unit 210 has a mouse, keyboard, button, trackball, joystick, or touch panel, for example. The input unit 210 transfers the instructions accepted from the operator to the system controller 290 described below.

The display unit 220 displays images generated by the X-ray diagnostic apparatus 1 and displays a graphical user interface (GUI) for accepting the instructions from the operator or the like. The display unit 220 is, for example, the fluoroscopic monitor or the system monitor illustrated in FIG. 1.

As illustrated in FIG. 2, the image processing apparatus 200a includes the A/D converting unit 230, the pixel value arithmetic unit 240, an image data generating unit 250, an image data storage unit 260, an image processing unit 270, an image correcting unit 280, and the system controller 290. The A/D converting unit 230 is connected to the FPD 16, converts analog signals input from the FPD 16 into digital signals, and transfers the converted digital signals (projection data) to the image data generating unit 250.

The pixel value arithmetic unit 240 sets a certain region of interest for original image data supplied from the image data generating unit 250 and calculates an average pixel value of the set region of interest. The pixel value arithmetic unit 240 supplies a comparison result between the calculated average pixel value and a certain threshold to the X-ray controller 20, thereby performing automatic brightness control (ABC). The control enables the X-ray diagnostic apparatus 1 to collect original image data of optimum brightness at all times.

The image data generating unit 250 generates original image data (X-ray image data) from the projection data supplied from the A/D converting unit 230. Specifically, the image data generating unit 250 successively stores data elements of the projection data supplied from the A/D converting unit 230 in the image data storage unit 260, thereby generating two-dimensional original image data. The image data storage unit 260 stores therein the original image data generated by the image data generating unit 250 and display images generated by the image processing unit 270.

The image processing unit 270 performs various pieces of image processing on the original image data stored in the image data storage unit 260 or image data corrected by the image correcting unit 280. The image processing unit 270, for example, performs image processing for display (such as spatial filter processing, window conversion, and gamma curve processing) on the image data corrected by the image correcting unit 280.

The image correcting unit 280 performs various corrections on the original image data generated by the image data generating unit 250. The image correcting unit 280, for example, performs corrections on the removal of interference fringes contained in the original image data, noise reduction, the removal of a scattered radiation component, resolution, or the like. The details of the corrections will be described in detail below.

The system controller 290 controls the operation of the entire X-ray image diagnostic system. The system controller 290, for example, controls the X-ray controller 20 under the instructions from the operator transferred from the input unit of the proximal control console or the input unit 210 and adjusts the voltage to be supplied to the X-ray tube 12, thereby controlling an X-ray radiation dose to be applied to the subject and on/off. The system controller 290, for example, controls the top board mechanism controller 18 under instructions from the operator to adjust the movement and tilting of the top board 14. The system controller 290, for example, controls the diaphragm controller 19 under instructions from the operator to adjust the opening of the diaphragm blades of the X-ray movable diaphragm 13, thereby controlling the irradiation range of the X-rays applied to the subject.

The system controller 290 controls the automatic brightness control by the pixel value arithmetic unit 240, original image data generation processing by the image data generating unit 250, image processing or analysis processing by the image processing unit 270, correction processing by the image correcting unit 280, or the like under instructions from the operator. The system controller 290 performs control so as to display the GUI for accepting instructions from the operator, the display images stored in the image data storage unit 260, or the like on the monitors of the display unit 220. The system controller 290 can also control the injection of the contrast medium by transmitting signals for starting and ending of the injection of the contrast medium to the injector.

The configuration of the X-ray diagnostic apparatus 1 has been described. The X-ray diagnostic apparatus 1 according to the present application under the above configuration can reduce radiation exposure while maintaining image quality. Specifically, the X-ray diagnostic apparatus 1 reduces radiation exposure while maintaining image quality by a configuration of the grid 15 and processing by the image correcting unit 280 described in detail below. First, a case will be described in which conventional techniques have difficulty in reducing radiation exposure while maintaining image quality. As described above, in an X-ray diagnostic apparatus, a grid is arranged on the detection face side of an X-ray detector in order to remove scattered radiation.

Figure 3:
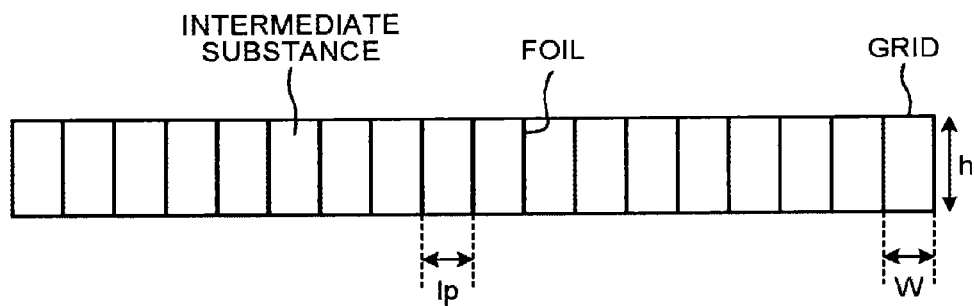
FIG. 3 is a diagram for illustrating a grid.

FIG. 3 is a diagram for illustrating the grid. FIG. 3 illustrates a sectional view of a grid. A parallel grid, in which foils are arranged in parallel, is described as an example in FIG. 3. As illustrated in FIG. 3, for example, the grid has intermediate substances that absorb less X-rays and the foils that absorb X-rays alternately. When X-rays having passed through a subject enter from the top of the drawing, direct radiation, which has nearly constant direction in the X-rays, passes through the intermediate substances to be detected by a detector. In contrast, scattered radiation contained in the X-rays enters the grid from various directions and is hence absorbed by the foils.

Such a grid sets a lattice density (LP/cm, for example) indicating how many pairs of an intermediate substance and a foil (lp: line pair) are contained in a unit length (cm, for example) and a lattice ratio "h:W" indicating the width "W" of the intermediate substance and the height (thickness) of the intermediate substance in accordance with various conditions. When the FPD is used as the X-ray detector, interference fringes caused by the pixels of the FPD and the lattice of the grid may occur. Specifically, interference fringes occur at a spatial frequency at which the lattice density of the grid is folded back at a Nyquist frequency of the FPD.

A general pixel size of the FPD used for X-ray diagnostic apparatuses is "0.140 mm to 0.150 mm," for example. The Nyquist frequency of the FPD is "33.3 (=10/0.15/2) LP/cm to 35.7 (=10/0.14/2) LP/cm." A general lattice density of the grid used for conventional X-ray diagnostic apparatuses is "40 LP/cm," "44 LP/cm," "60 LP/cm," or the like. When using such an FPD and grid in combination, the lattice densities of the grid "40 LP/cm," "44 LP/cm," or "60 LP/cm" are folded back at the Nyquist frequency of the FPD "33.3 LP/cm to 35.7 LP/cm" to produce interference fringes. For the lattice density "40 LP/cm," for example, interference fringes occur at "26.6 (=33.3−6.7 (=40−33.3)) LP/cm to 31.4 (=35.7−4.3 (=40−35.7)) LP/cm. For the lattice densities "44 LP/cm" and "60 LP/cm," similarly, interference fringes occur at "22.6 LP/cm to 27.4 LP/cm" and "6.6 LP/cm to 11.4 LP/cm," respectively.

In view of the above circumstances, as described above, the conventional techniques match the lattice density of the grid with the pixel pitch of the FPD or use a grid having a lattice density high enough not to be able to convert input signals even by the FPD, thereby inhibiting such interference fringes from occurring. However, using such a grid brings about various restrictions, which may cause difficulty in reducing radiation exposure while maintaining image quality.

When the lattice density of the grid is matched with the pixel pitch of the FPD, for example, extremely high pitch accuracy is required, and aluminum (Al), which is high in thickness accuracy and rigidity, is required to be used as the intermediate substance. Under circumstances where the maximum lattice density stably manufacturable by the current technique is "80 LP/cm," for example, when adopting a grid having such a lattice density, Al is required to be used as the intermediate substance in order to freely designate the lattice ratio. When thus using Al as the intermediate substance of the grid, the transmittance of the direct radiation decreases compared to a case in which fiber such as paper is used, leading to deterioration in image quality.

A grid used when inhibiting the occurrence of interference fringes using the grid having a high lattice density generally has "lattice density: 80 LP/cm, lattice ratio: 15:1, intermediate substance: Al." When using such a grid and at the same time attempting to reduce an exposure dose, image quality decreases. In attempting to reduce the exposure dose by "reducing the grid lattice ratio," for example, the height (thickness) of the intermediate substance is reduced, and the ratio of the scattered radiation passing through the grid increases, thus increasing noise and decreasing contrast. In attempting to reduce the exposure dose by "reducing the radiation dose of fluoroscopy and photography," a signal component decreases, whereby quantum noise increases. In attempting to reduce the exposure dose by "increasing the radiation quality of fluoroscopy and photography (increasing the tube voltage or increasing the thickness of a quality filter)," the ratio of the scattered radiation increases, whereby the signal component decreases.

Thus, the conventional techniques have difficulty in achieving both the prevention of deterioration in image quality and a reduction in the radiation dose while using a grid for inhibiting the occurrence of interference fringes. In view of such circumstances, the X-ray diagnostic apparatus 1 according to the first embodiment is configured to be able to reduce the radiation dose while providing X-ray images with no occurrence of interference fringes, with reduced occurrence of noise, and with a reduced contrast decrease.

Figure 4:
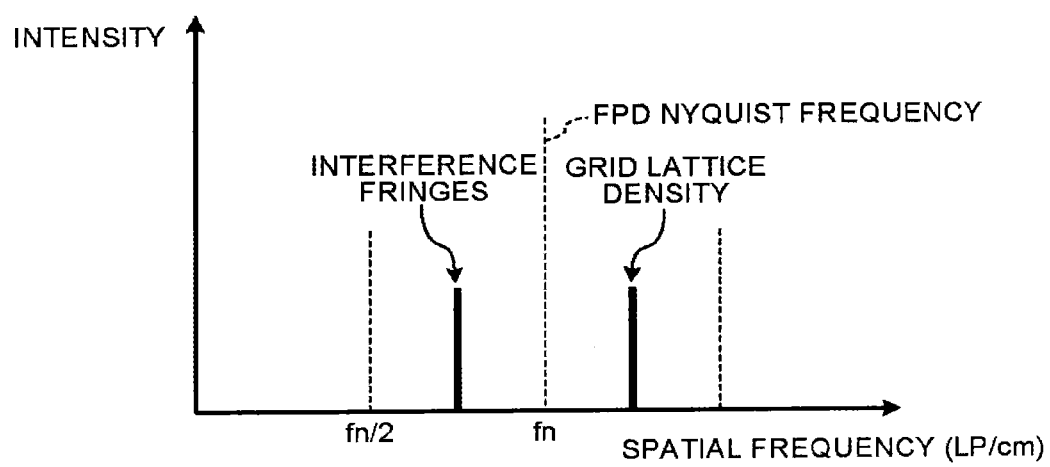
FIG. 4 is a diagram for illustrating a lattice density of a grid according to the first embodiment.

The X-ray diagnostic apparatus 1 according to the first embodiment reduces the radiation dose while maintaining image quality by the grid 15 and the image correcting unit 280, which will be described in detail below. Specifically, the grid 15 according to the first embodiment has a lattice density so that the frequency of interference fringes caused by interference with the pixels of the FPD is within a range of the Nyquist frequency of the FPD to half the Nyquist frequency. FIG. 4 is a diagram for illustrating the lattice density of the grid 15 according to the first embodiment. In FIG. 4, the vertical axis shows intensity, whereas the horizontal axis shows spatial frequency (LP/cm).

As illustrated in FIG. 4, for example, the interference fringes caused by the pixels of the FPD and the lattice of the grid occur at a spatial frequency at which the lattice density of the grid is folded back at the Nyquist frequency "fn" of the FPD 16. As illustrated in FIG. 4, the grid 15 has a lattice density so as to produce the interference fringes within a range of "fn/2," which is half the Nyquist frequency "fn," to the Nyquist frequency "fn." The grid 15 has a lattice density so as to cause the frequency of the interference fringes to occur at a frequency nearer to the Nyquist frequency "fn."

When the pixel size of the FPD is "0.148 mm," for example, the Nyquist frequency of the FPD is "33.8 LP/cm." In such a case, the grid 15 has a lattice density so as to produce the interference fringes at a spatial frequency nearer to the Nyquist frequency "33.8 LP/cm" within "16.9 to 33.8 LP/cm." In other words, the grid 15 has a lattice density nearer to "33.8 LP/cm" within a range of "33.8 to 50.7 LP/cm." Thus, the X-ray diagnostic apparatus 1 according to the first embodiment is configured to facilitate later interference fringe removal processing by designing the grid 15 so as to produce the interference fringes at a certain spatial frequency.

Figure 5:
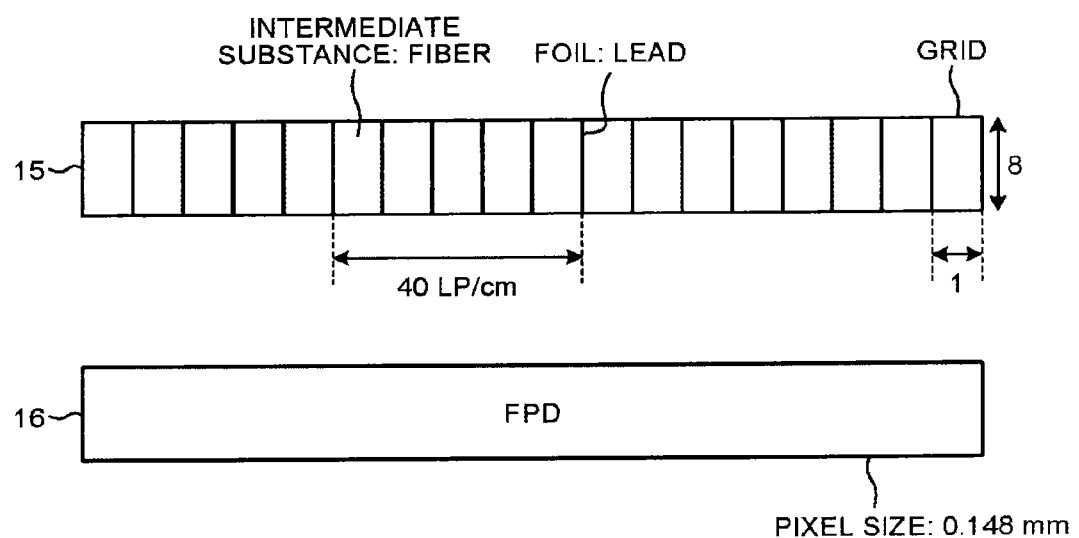
FIG. 5 is a diagram illustrating an example of the grid according to the first embodiment.

Furthermore, the grid 15 is formed with a lattice ratio and of an intermediate substance that cause direct radiation contained in the X-rays having passed through the subject to pass therethrough easily. The grid 15, for example, has a lattice ratio of (h:w=6:1 to 10:1) and has fiber as the intermediate substance. This configuration can produce an X-ray image having similar image quality to a case in which a conventional grid (a grid configured by lattice density: 80 LP/cm, lattice ratio: 15:1, intermediate substance: Al, for example) is used at a low radiation dose. The following describes an example with reference to FIG. 5. FIG. 5 is a diagram illustrating an example of the grid 15 according to the first embodiment.

As illustrated in FIG. 5, for the FPD 16 having a pixel size of "0.148 mm," the grid 15 is configured by "lattice density: 40 LP/cm, lattice ratio: 8:1, intermediate substance: fiber, foil: lead." When performing fluoroscopy and photography on a subject having a thickness of "20 cm" with a similar radiation dose and radiation quality to conventional ones using such a grid 15, a direct radiation dose increases by "15 to 20%" compared to the conventional grid of "lattice density: 80 LP/cm, lattice ratio: 15:1, intermediate substance: Al, foil: lead." This increase means that the signal component of a collected X-ray image increases by "15 to 20%." Thus, the X-ray diagnostic apparatus 1 according to the first embodiment assigns this increment of the signal component to a reduction in radiation dose, thereby reducing the exposure dose.

As an example, the X-ray diagnostic apparatus 1 according to the first embodiment includes the grid 15 and performs fluoroscopy and photography on the subject having a thickness of "20 cm" with "80% of the conventional radiation dose" and "a tube voltage of +10 kV with respect to the conventional radiation quality." When performing fluoroscopy and photography with such conditions, the direct radiation dose decreases to "85 to 90%" compared to a case of performing fluoroscopy and photography with "conventional grid/conventional radiation dose/conventional radiation quality." This decrease indicates that the decrement is greatly smaller than the decrease in the direct radiation amount to "75%" in "conventional grid/80% radiation dose/+10 kV radiation quality," meaning that a substantial part of the signal component can be maintained. When performing fluoroscopy and photography with the above conditions, a radiation dose on the surface of the subject, which is an indication of the exposure dose, decreases to "about 60%" compared to the case when performing fluoroscopy and photography with "conventional grid/conventional radiation dose/conventional radiation quality." Using the grid 15 can thus reduce the exposure dose.

However, when using the grid 15, interference fringes occur around a spatial frequency of "27.6 LP/cm." When performing fluoroscopy and photography with the above conditions, the radiation dose of the total X-rays increases by "5 to 10%" compared to the case when performing fluoroscopy and photography with "conventional grid/conventional radiation dose/conventional radiation quality." This increase is caused by an about 25% increase in the scattered radiation, resulting in an about 15% decrease in S/N ratio and a contrast decrease.

Figure 6:
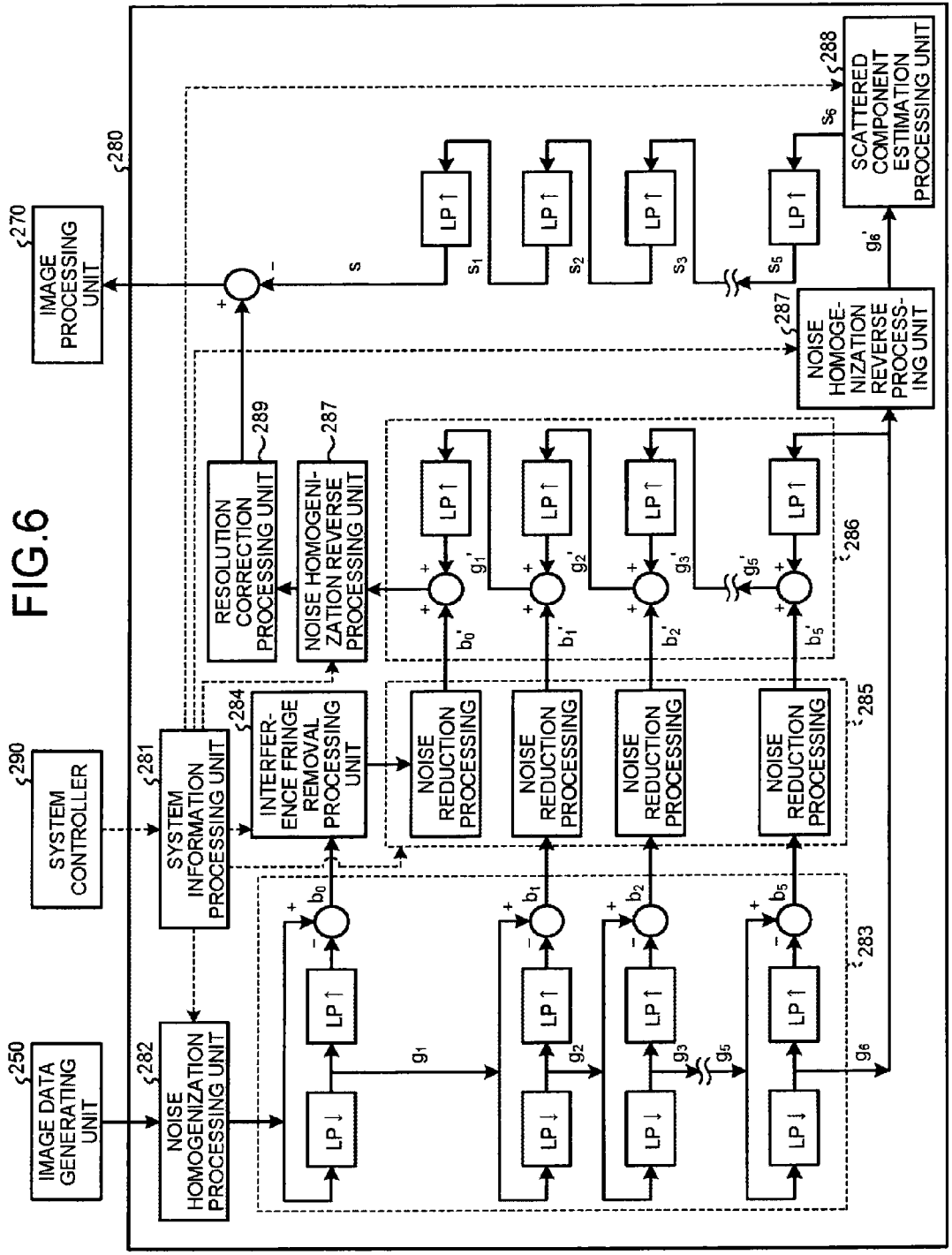
FIG. 6 is a diagram illustrating an example of the configuration of an image correcting unit according to the first embodiment.

Accordingly, the X-ray diagnostic apparatus 1 according to the first embodiment causes the image correcting unit 280 to correct the above decreases, thereby improving the image quality decreased owing to the use of the grid 15. FIG. 6 is a diagram illustrating an example of the configuration of the image correcting unit 280 according to the first embodiment. As illustrated in FIG. 6, included are a system information processing unit 281, a noise homogenization processing unit 282, a frequency band data generating unit 283, an interference fringe removal processing unit 284, a noise reduction processing unit 285, a frequency band data synthesizing unit 286, a noise homogenization reverse processing unit 287, a scattered component estimation processing unit 288, and a resolution correction processing unit 289. The image correcting unit 280 performs various pieces of correction processing on the original image data generated by the image data generating unit 250 and transmits the corrected image data to the image processing unit 270.

The system information processing unit 281 controls pieces of processing by the respective units of the image correcting unit 280 under the control of the system controller 290. Specifically, the system information processing unit 281 controls the respective units described below, thereby controlling noise homogenization processing, interference fringe removal processing, noise reduction processing, noise homogenization reverse processing, scattered component estimation processing, and resolution correction processing.

Figure 7:
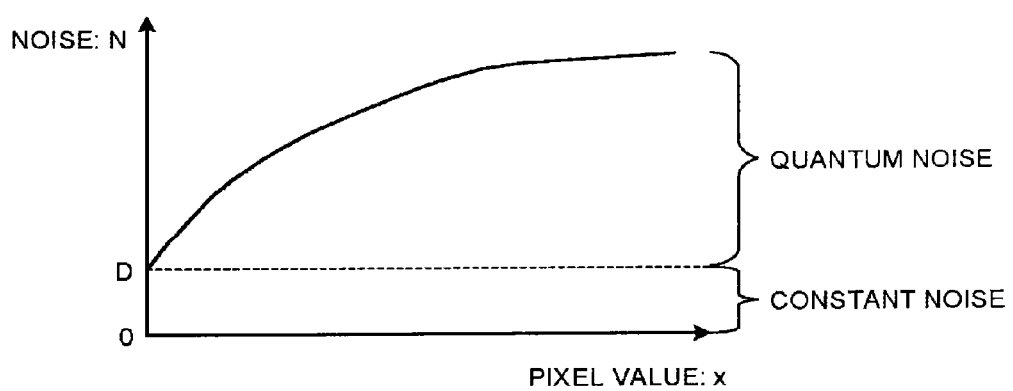
FIG. 7 is a diagram for illustrating noise according to the first embodiment.

The noise homogenization processing unit 282 homogenizes noise of each pixel contained in the original image data. When using the FPD as the X-ray detector, the noise contained in an X-ray image changes in accordance with a pixel value. FIG. 7 is a diagram for illustrating the noise according to the first embodiment. As illustrated in FIG. 7, for example, noise "N" contained in an X-ray image includes noise "D" that is constant regardless of the pixel value "x" and quantum noise of X-ray photon origin that is proportional to the square root of the incident radiation dose of the FPD, that is, the square root of the pixel value "x."

As illustrated in FIG. 7, the noise of an image changes in accordance with a change in the pixel value. The X-ray diagnostic apparatus 1 causes the noise homogenization processing unit 282 to perform the noise homogenization processing that converts the noise into a constant value regardless of the pixel value "x" in order to increase the effect of the noise reduction processing by the noise reduction processing unit 285 described below.

Specifically, the noise homogenization processing unit 282 makes the noise constant by differentiating a noise estimation equation obtained by representing the noise curve illustrated in FIG. 7 with a function of the pixel value "x" with respect to the pixel value "x" and taking the inverse thereof. The FPD 16 has some collection modes that vary in the combination of the number of pixels collected as one pixel, sensitivity setting, and the like. In view of this, the noise homogenization processing unit 282 determines the noise estimation equation for each collection mode and performs the noise homogenization processing for each. The noise homogenization processing unit 282, for example, acquires information on fluoroscopy or photography, visual field size, image resolution setting, and the like from the system information processing unit 281 and determines the collection mode based on the acquired information to perform the noise homogenization processing.

Returning back to FIG. 6, the frequency band data generating unit 283 converts original image data based on X-rays detected by the FPD 16 into a plurality of pieces of frequency band data. Specifically, the frequency band data generating unit 283 converts the original image data based on the X-rays having passed through the grid 15 and detected by the FPD 16 into the pieces of frequency band data and background data (a piece of background data, for example). More specifically, the frequency band data generating unit 283 generates the pieces of frequency band data containing respective certain frequency bands and a piece of background data from the original image data whose noise has been homogenized by the noise homogenization processing unit 282. As illustrated in FIG. 6, for example, the frequency band data generating unit 283 performs low pass filter (LPF) processing step by step and takes the difference with a previous LPF processed image, thereby generating pieces of frequency band data containing respective different frequency bands.

As an example, the frequency band data generating unit 283 first performs the LPF processing on the noise-homogenized original image data in a first stage LP↓, thereby extracting low-frequency data. In order to speed up the following processing, the frequency band data generating unit 283 performs down-sampling processing in the LP↓. As an example, the frequency band data generating unit 283 first drops every other horizontal pixels from the LPF processed original image data (low-frequency data) and then drops every other vertical pixels, thereby generating low-resolution image data $g_1$ whose image size has been reduced to ¼.

The frequency band data generating unit 283 sends the low-resolution image data $g_1$ to a second stage and performs up-sampling processing and the LPF processing in an LP↑, thereby generating low-frequency data that is of the same size as the original image data and is LPF processed. The frequency band data generating unit 283, for example, first interpolates "0" to every other horizontal pixels and then interpolates "0" to every other vertical pixels of the low-resolution image data $g_1$ and performs LPF processing with the elements of the first LPF quadrupled on the low-resolution image data $g_1$. The frequency band data generating unit 283 then takes the difference between the original image data and the low-frequency data for each pixel by an adder, thereby generating frequency band data $b_0$. For the LPF processing by the frequency band data generating unit 283, a Gaussian filter of about 5×5 can be used.

The frequency band data generating unit 283 performs the processing of the second and subsequent stages in the same manner as the processing at the first stage described above. Image data to be processed at each stage is the low-resolution image data generated at the previous stage. In other words, the image data to be processed at the second stage is the low-resolution image data $g_1$, and after that, pieces of low-resolution image data $g_2$ to $g_5$ generated at the respective stages are pieces of image data to be processed at the respective subsequent stages. The frequency band data generating unit 283 generates pieces of frequency band data $b_1$ to $b_5$ in the same manner as the first stage using the low-resolution image data $g_2$ to $g_5$ at the respective stages. Thus, the frequency band data generating unit 283 generates the pieces of stepwise frequency band data and background data $g_6$ that contains only background as information. Although FIG. 6 illustrates a case in which the frequency band data generating unit 283 performs the six-stage processing, embodiments are not so limited, and the processing can be performed with any number of stages.

Figure 8A:
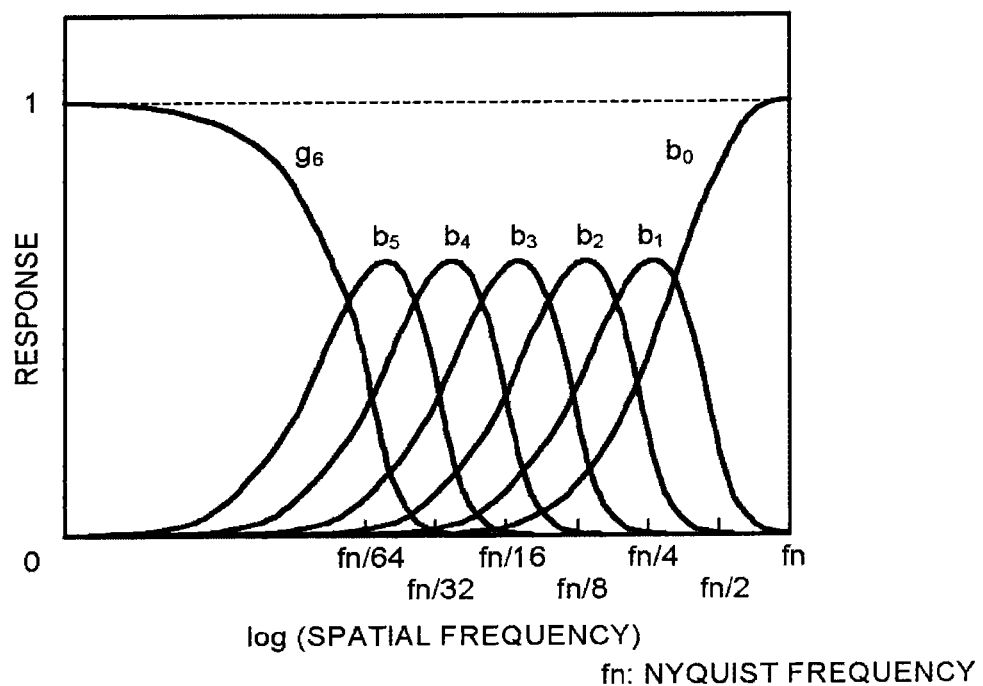
FIG. 8A is a diagram illustrating an example of a processing result by a frequency band data generating unit according to the first embodiment.
Figure 8B:
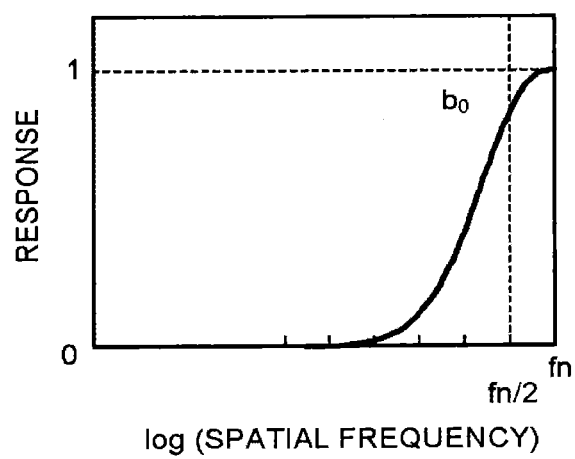
FIG. 8B is a diagram illustrating an example of the processing result by the frequency band data generating unit according to the first embodiment.

FIG. 8A and FIG. 8B are diagrams illustrating an example of a processing result by the frequency band data generating unit 283 according to the first embodiment. FIG. 8A illustrates frequency characteristics of the frequency band data $b_0$ to $b_5$ and the background data $g_6$. FIG. 8B illustrates a frequency characteristic of only the frequency band data $b_0$. As illustrated in FIG. 8A, for example, the frequency band data generating unit 283 generates the frequency band data $b_0$ to $b_5$ that have different frequency bands. As illustrated in FIG. 8B, the frequency band data $b_0$ contains almost all components from "fn/2," which is half the Nyquist frequency of the FPD, to the Nyquist frequency "fn." Thus, using the grid 15 produces interference fringes within a range of "fn/2" to "fn," the frequency band data $b_0$ contains almost all components corresponding to the interference fringes. The pieces of frequency band data $b_0$ to $b_5$ illustrated in FIG. 8A contains components of the subject corresponding to the respective frequency bands and also contains noise. The pieces of noise in the frequency band data $b_0$ to $b_5$ and the background data $g_6$ are homogenized by the noise homogenization by the noise homogenization processing unit 282. When the noise characteristics of the pieces of frequency band data $b_0$ to $b_5$ are different from that of the original image data and further different from each other, processing that converts the previous-stage noise homogenization and the subsequent-stage noise homogenization is applied to the low-resolution image data $g_1$ to $g_5$.

Returning back to FIG. 6, the interference fringe removal processing unit 284 removes interference fringes contained in one or some pieces of frequency band data among the pieces of frequency band data. Specifically, the interference fringe removal processing unit 284 removes the components corresponding to the interference fringes within a range of "fn/2" to "fn." As described above, the frequency band data $b_0$ generated by the frequency band data generating unit 283 contains almost all components corresponding to the interference fringes. Given this situation, the interference fringe removal processing unit 284 performs the interference fringe removal processing on the frequency band data $b_0$ as illustrated in FIG. 6.

FIG. 9A and FIG. 9B are diagrams for illustrating the interference fringe removal processing by the interference fringe removal processing unit 284 according to the first embodiment. FIG. 9A illustrates an example of the processing by the interference fringe removal processing unit 284, whereas FIG. 9B illustrates an example of LPF applied to the interference fringe removal processing unit 284.

As illustrated in FIG. 9A, for example, in the frequency band data $b_0$ to be processed, the column direction of pixels contained in the frequency band data $b_0$ is set as an x direction, whereas the row direction is set as a y direction. A case will be described as an example in which the interference fringes caused by the grid 15 occur in parallel with the y direction (the arranging direction of the interference fringes matches the x direction) as illustrated in FIG. 9A.

In such a case, the interference fringe removal processing unit 284 first performs LPF processing in the x direction to generate x-direction LPF processed image. Specifically, the interference fringe removal processing unit 284 applies a one-dimensional spatial filter that passes low-frequency components to the x direction of the frequency band data $b_0$, thereby generating the x-direction LPF processed image in which the components of the interference fringes are mainly removed. The LPF applied by the interference fringe removal processing unit 284 has a kernel size of (x,y)=(31, 1), for example, and has such a frequency characteristic as shown in FIG. 9B.

When the interference fringes occur at "27.6 LP/cm" by using the grid 15, for example, the interference fringe removal processing unit 284 applies LPF processing having a characteristic that abruptly drops from "1" to "0" immediately before the frequency of the interference fringes "27.6 LP/cm" as illustrated in FIG. 9B. This processing removes frequency band components having a gain of 0 and leaves frequency band components having a gain of 1 without being influenced by the LPF. This processing enables the interference fringe removal processing unit 284 to produce the x-direction LPF processed image in which the components of the interference fringes are mainly removed. Thus, the interference fringe removal processing unit 284 selectively removes the components of the interference fringes within a range of half the Nyquist frequency fn to the Nyquist frequency fn. Frequency bands of images (parts indicating the internal morphology of a subject or the like) required for diagnosis are generally sufficiently smaller than half the Nyquist frequency fn. Consequently, even when the gain is dropped to 0 immediately before the frequency of the interference fringes as illustrated in FIG. 9B, there is almost no influence on the images required for diagnosis.

The collection of image data by the FPD 16 includes, in addition to the mode that constitutes image data with output from one detection element contained in the FPD 16 as one pixel as described above, a mode that averages electric charges detected by a 2×2 or 3×3 detection elements to form one pixel. The frequency of interference fringes varies by the mode. Some modes may produce no interference fringes. The type of the mode is sent to the system information processing unit 281 by the system controller 290. The system information processing unit 281 stores therein in advance optimum kernel sizes and gains for respective modes and sends a kernel size and gain corresponding to the type of the mode sent from the system controller 290 to the interference fringe removal processing unit 284. The interference fringe removal processing unit 284 performs LPF processing using the kernel size and gain sent from the system information processing unit 281. In a mode that produces no interference fringes, the processing by the interference fringe removal processing unit 284 may be skipped.

After generating the x-direction LPF processed image as described above, the interference fringe removal processing unit 284 takes the difference between the frequency band data $b_0$ and the x-direction LPF processed image, thereby producing an interference fringe image mainly constituted by the components of the interference fringes. The interference fringe removal processing unit 284 then performs y-direction LPF processing on the interference fringe image. In the y-direction LPF processing, the same kernel size ((x,y)=(1,31), for example) and gain as those of the x-direction LPF processing may be used, or any kernel size and gain that pass frequency components different from those of the x-direction LPF processing such as only lower frequency components may be used. This processing causes the interference fringe removal processing unit 284 to produce an interference fringe image that represents the components of the interference fringes more accurately.

After producing the interference fringe image that represents the components of the interference fringes more accurately by the y-direction LPF processing as described above, the interference fringe removal processing unit 284 takes the difference between the frequency band data $b_0$ and the interference fringe image, thereby producing a processed image in which the interference fringes are removed from the frequency band data $b_0$. After thus producing the interference-fringe removed processed image, the interference fringe removal processing unit 284 sends the produced processed image to the noise reduction processing unit 285.

Returning back to FIG. 6, the noise reduction processing unit 285 reduces noise contained in the frequency band data. Specifically, as illustrated in FIG. 6, the noise reduction processing unit 285 reduces the noise contained in the frequency band data $b_0$ in which the interference fringes have been removed by the interference fringe removal processing unit 284 and the pieces of frequency band data $b_1$ to $b_5$ generated by the frequency band data generating unit 283. The noise reduction processing unit 285 can use various methods as processing for reducing the noise in the respective pieces of frequency band data. The noise reduction processing unit 285 can use a coherent filter disclosed in Japanese Patent No. 4170767, for example.

The coherent filter can effectively reduce noise while maintaining resolution. The coherent filter is characterized in that a weighted average of local pixels such as neighboring 3×3 pixels is calculated, and based on that the weighted average value is set as the value of a local central pixel, pieces of weight of respective peripheral pixels are changed in accordance with the degree of similarity between the central pixel and the peripheral pixels. The degree of similarity in this context is an index indicating the degree of possibility that pixels are of pieces of anatomically similar tissue, specifically, pieces of brain tissue (capillary vessels) under the domination of the same cerebral artery; high weight is given to a pixel having a high degree of similarity, whereas low weight near zero is given to a pixel having a low degree of similarity, thereby enabling degradation of spatial resolution to be inhibited while achieving noise suppression.

The frequency band data $b_0$ to $b_5$ to be subjected to the noise reduction processing by the noise reduction processing unit 285 have been subjected to the noise homogenization processing, and they have noise of the same magnitude other than the signal components. Owing to this situation, a part that differs in pixel value in the original image data and is not subjected to the coherent processing is subjected to the processing, thus improving a noise reduction effect.

When performing fluoroscopy on the subject, in addition to the processing by the coherent filter, processing for reducing noise in a time direction may be performed on the frequency band data. As such processing, a process disclosed in Japanese Patent Application No. 2011-250066 or the like may be applied, for example. After performing the above noise reduction processing, the noise reduction processing unit 285 sends frequency band data $b_0'$ to $b_5'$ obtained by reducing the noise of the frequency band data $b_0$ to $b_5$ to the frequency band data synthesizing unit 286.

The frequency band data synthesizing unit 286 synthesizes the pieces of frequency band data after being processed by the respective processing units to generate image data. Specifically, the frequency band data synthesizing unit 286 successively synthesizes the background data $g_6$ and the noise-reduced frequency band data $b_0'$ to $b_5'$ to generate image data of the same size as the original image data with reduced interference fringes and noise. The frequency band data synthesizing unit 286, for example, performs up-sampling processing (that first interpolates "0" to every other horizontal pixels and then interpolates "0" to every other vertical pixels) on the background data $g_6$ in an LP↑ at a first stage (the lowermost stage in the drawing) to perform the same LPF processing as the up-sampling processing of the frequency band data generating unit 283, thereby causing the background data $g_6$ to have the same size as the frequency band data $b_5'$. The frequency band data synthesizing unit 286 adds the frequency band data $b_5'$ and the background data $g_6$ having the same size by an adder pixel by pixel to generate addition data $g_5'$.

The frequency band data synthesizing unit 286 performs the above up-sampling processing and LPF processing on the generated addition data $g_5'$, thereby causing the addition data $g_5'$ to have the same size as the frequency band data $b_4'$ and adds the frequency band data $b_4'$ thereto to generate addition data $g_4'$. Similarly, the frequency band data synthesizing unit 286 successively performs the size increase of the addition data and the addition of the frequency band data to generate image data of the same size as the original image data with reduced interference fringes and noise.

As described above, the X-ray diagnostic apparatus 1 performs the interference fringe removal processing and the noise reduction processing on the original image data based on the X-rays having passed through the grid 15. The X-ray diagnostic apparatus 1 further performs the resolution correction processing and scattered component correction processing. Incidentally, the X-ray diagnostic apparatus 1 performs the noise homogenization processing on the original image data in order to increase the effect of noise reduction. In order to accurately perform the resolution correction processing and the scattered component correction processing, the X-ray diagnostic apparatus 1 performs the noise homogenization reverse processing by the noise homogenization reverse processing unit 287.

Specifically, in order to make pixel values pixel values proportional to the radiation dose, the noise homogenization reverse processing unit 287 performs the noise homogenization reverse processing by a conversion equation obtained by solving a noise homogenization equation for the pixel value "x."

The noise homogenization reverse processing unit 287, for example, applies the conversion equation obtained by solving the noise homogenization equation for the pixel value "x" to the image data generated by the frequency band data synthesizing unit 286 and the background data $g_6$, thereby restoring the pixel values of the respective pieces of data to values proportional to the radiation dose.

The scattered component estimation processing unit 288 (also called the correction processing unit) corrects a scattered radiation component of the original image data based on a scattered radiation component contained in the X-rays having passed through the grid 15 and a scattered radiation component contained in X-rays having passed through a grid that removes scattered radiation to a larger extent than the grid 15. Specifically, the scattered component estimation processing unit 288 estimates the difference between the scattered radiation component contained in the X-rays having passed through the grid 15 and the scattered radiation component contained in the X-rays having passed through a target grid ("lattice density: 44 LP/cm, lattice ratio: 15:1, intermediate substance: fiber," for example) having higher scattered radiation removal capability than the grid 15 and corrects the scattered radiation component based on the estimated difference. More specifically, the scattered component estimation processing unit 288 corrects a scattered radiation component contained in the background data $g_6$ or data under generation after being processed by the respective processing units based on the estimated difference.

Described first is the estimation of the scattered radiation component contained in X-ray image data performed by the scattered component estimation processing unit 288. The X-ray image data includes a primary X-ray image as image data by primary X-rays and a scattered radiation image as image data by the scattered radiation. A function that is subjected to convolutional integration on the primary X-ray image to produce the scattered radiation image is defined as a scattering function. Thus, the X-ray image data is represented as a summation of the primary X-ray image, the convolutional integration of the primary X-ray image and the scattering function, and a direct radiation image.

The scattering function varies by the tube voltage, an irradiation field area, and a subject thickness. Accordingly, the scattering function is determined in advance with respect to various conditions on the tube voltage, the irradiation field area, and the subject thickness by using a phantom, for example. The determined scattering function is stored in a scattering function correspondence table. The subject thickness can be estimated by an experimental equation using the tube voltage, time integration of the tube current, an X-ray focus-to-X-ray detector distance, a set radiation dose, and a statistical amount of the pixel value such as an average pixel value. Accordingly, such an experimental equation is determined in advance. The scattering function correspondence table and the experimental equation are stored in a memory of the system controller 290, the image correcting unit 280, or the scattered component estimation processing unit 288 or the image data storage unit 260.

The scattering function is determined based on the X-ray conditions at the X-ray image data collection, the subject thickness determined by the experimental equation, and the scattering function correspondence table. An equation represented as a summation of direct radiation images is Fourier transformed, the Fourier transformation of the primary X-ray image is solved, and inverse Fourier transformation is performed to produce the primary X-ray image, that is, an image (hereinafter, called a scattered radiation reduced image) whose scattered radiation component has been reduced by the scattered radiation correction processing.

However, the above process cannot change the scattering function in accordance with the position of pixels in the X-ray image data. Accordingly, in X-ray image data containing a part (hereinafter called a direct radiation component) in which there is no subject and X-rays directly enter or X-ray image data having a non-direct radiation component having passed through a part (hereinafter, called a thin body thickness part) that is partially thin in a subject, the scattered radiation component cannot be appropriately reduced.

Figure 10:
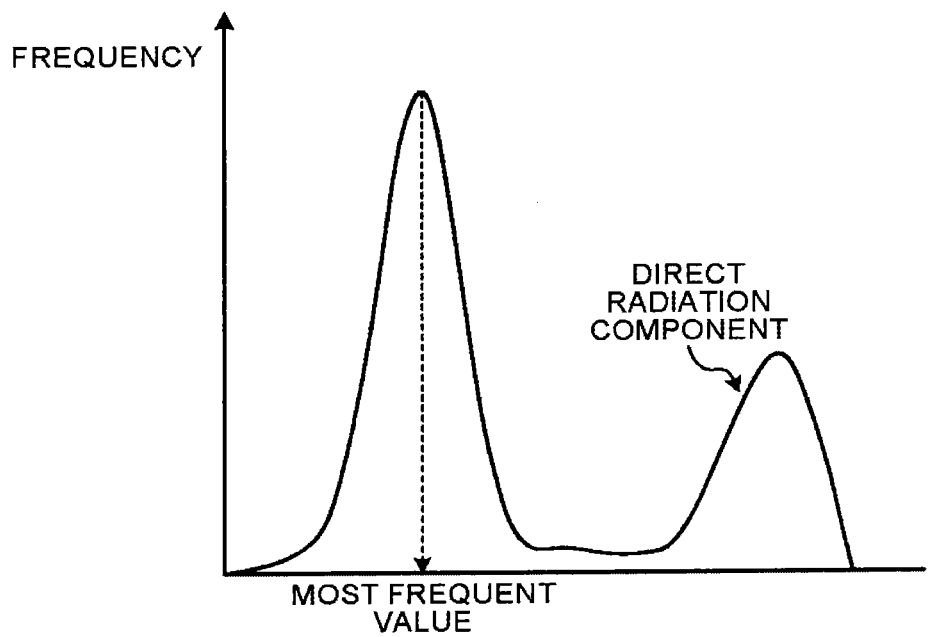
FIG. 10 is a diagram illustrating an example of the distribution of a plurality of pixel values constituting X-ray image data according to the first embodiment.

The scattered radiation component may be excessively corrected, for example (hereinafter, called overcorrection). In order to prevent overcorrection, pixel values higher than a standard value among a plurality of pixel values constituting X-ray image data are converted into pixel values lower than the standard value. FIG. 10 is a diagram illustrating an example of the distribution (pixel value distribution) of a plurality of pixel values constituting the X-ray image data according to the first embodiment. In the pixel value distribution, the direct radiation component involves no attenuation of radiation dose caused by passing through the subject and hence is present in the range of higher pixel values than the non-direct radiation component.

The non-direct radiation component having passed through the thin body thickness part involves less attenuation of radiation dose caused by passing through the subject similarly to the direct radiation component and hence is present in the range of higher pixel values than the non-direct radiation component. The following describes only X-ray image data having the direct radiation component for simplifying description. X-ray image data having the non-direct radiation component having passed through the thin body thickness part also has the same effect.

The scattered component estimation processing unit 288 sets the most frequent value of the pixel values constituting the X-ray image data as a representative value and multiplies it by a certain constant to determine the standard value. Alternatively, the scattered component estimation processing unit 288 uses an average value or a median value of a plurality of pixel values contained in a region of interest input from the outside or registered in advance as the representative value to determine the standard value. Alternatively, the scattered component estimation processing unit 288 uses a target pixel value of automatic brightness control of fluoroscopy or a target pixel value of automatic exposure control of photography as the representative value to determine the standard value. The standard value can be changed under the direction of an operator or the like.

The scattered component estimation processing unit 288 stores therein a pixel value conversion table. The pixel value conversion table shows a correspondence relation between pixel values before conversion and pixel values after conversion. The scattered component estimation processing unit 288 converts pixel values higher than the standard value into pixel values lower than the standard value among the pixel values constituting the X-ray image data based on the pixel value conversion table and the standard value. The scattered component estimation processing unit 288, for example, converts the pixel values of pixels having the direct radiation component in the X-ray image data into lower pixel values.

More specifically, the pixel value conversion table, for example, represents the following correspondence relation between the pixel values before conversion and the pixel values after conversion. The pixel value conversion table may show a correspondence relation for performing identical transformation on pixel values not more than the standard value among the pixel values of the X-ray image data or may not change the pixel values not more than the standard value among the pixel values of the X-ray image data. Furthermore, the pixel value conversion table shows a correspondence relation for converting pixel values not less than the standard value and not more than the double of the standard value among the pixel values of the X-ray image data into pixel values not more than the standard value. The pixel value conversion table shows a correspondence relation for converting pixel values not less than the double of the standard value among the pixel values of the X-ray image data into zero. By converting the pixel values not less than the standard value and not more than the double of the standard value into the lower pixel values, the occurrence of artifacts can be inhibited in a scattered radiation image generated by scattered radiation image calculation described below using the image (hereinafter, called a converted image) obtained by converting the pixel values of the X-ray image data.

The scattered component estimation processing unit 288 converts the converted imaged into the scattered radiation image in the X-ray image data based on the scattering function. Specifically, the scattered component estimation processing unit 288 produces a Fourier transform of the converted image. The scattered component estimation processing unit 288 generates a Fourier transform of the scattering function. The scattered component estimation processing unit 288 then divides the Fourier transform of the scattering function by a summation of the Fourier transform and 1 (hereinafter, the result of the division will be referred to as a scattering function term). The scattered component estimation processing unit 288 then multiplies the Fourier transform of the converted image by the scattering function term to produce a Fourier transform of the scattered radiation image. Finally, the scattered component estimation processing unit 288 applies inverse Fourier transformation to the Fourier transform of the scattered radiation image to produce the scattered radiation image.

Thus, the scattered component estimation processing unit 288 can produce the scattered radiation image even for the X-ray image data containing the direct radiation and the X-ray image data having the non-direct radiation component having passed through the part (thin body thickness part) that is partially thin in the subject with a reduced amount of calculation and without overcorrection.

The scattered component estimation processing unit 288 stores therein the scattering function of the grid 15 and the scattering function of the target grid ("lattice density: 44 LP/cm, lattice ratio: 15:1, intermediate substance: fiber," for example) having higher scattered radiation removal capability than the grid 15. In the calculation of the scattering function term, the difference between the Fourier transform of the scattering function of the grid 15 and the Fourier transform of the scattering function of the target grid is used in place of the Fourier transform of the scattering function, thereby approximating a Fourier transform of the difference between the scattered radiation component by the grid 15 and the scattered radiation component of the target grid. Applying inverse Fourier transformation thereto produces the scattered radiation image of the difference between the grid 15 and the target grid.

In order to perform the extraction of the scattering function, the system information processing unit 281 performs the following processing. First, the system information processing unit 281 stores therein a database including a scattering function spr0 (x,y) of the grid 15 actually measured in advance for each tube voltage, irradiation field area, and subject thickness and a scattering function spr1 (x,y) of the target grid having higher scattered radiation removal capability than the grid 15 and an experimental equation for estimating the subject thickness from the tube voltage, the time integration of the tube current, the X-ray focus-to-X-ray detector distance, the set radiation dose, and the statistical amount of the pixel value. Along with the performance of fluoroscopy and photographing, the system controller 290 sends the tube voltage, the time integration of the tube current, the X-ray focus-to-X-ray detector distance, the set radiation dose, and the statistical amount of the pixel value such as an average pixel value as system information to the image correcting unit 280.

The system information processing unit 281 estimates the subject thickness using the tube voltage, the time integration of the tube current, the X-ray focus-to-X-ray detector distance, the set radiation dose, and the statistical amount of the pixel value contained in the system information sent from the system controller 290 and the experimental equation. The system information processing unit 281 then extracts spr0 (x,y) and spr1 (x,y) corresponding to the estimated subject thickness and the tube voltage and the irradiation field area contained in the system information sent from the system controller 290 from the database.

Figure 11:
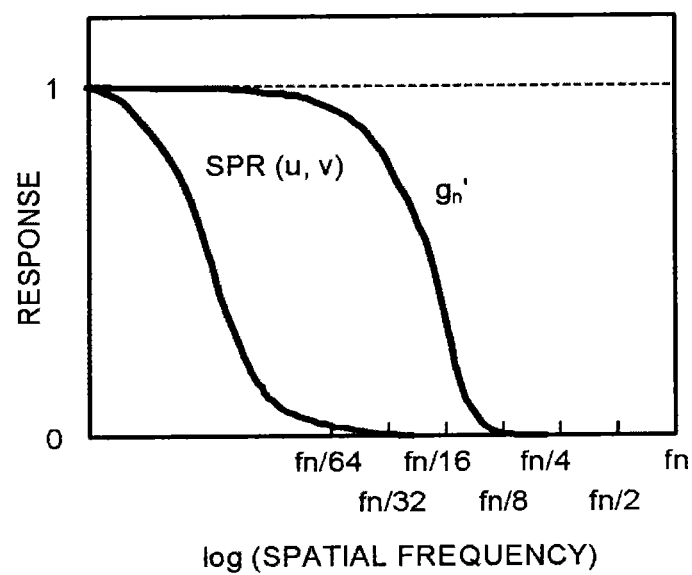
FIG. 11 is a diagram for illustrating image data to be processed by a scattered component estimation processing unit according to the first embodiment.

Although the example in FIG. 6 illustrates a case of generating a scattered component estimation image using the background data $g_6$, embodiments are not so limited, and addition data $g_n'$ may also be used. FIG. 11 is a diagram for illustrating image data to be processed by the scattered component estimation processing unit 288 according to the present embodiment. FIG. 11 illustrates an example of a relation between the addition data $g_n'$ and SPR1 (u,v) obtained by performing Fourier transformation on the scattering function spr1 (x,y). As illustrated in FIG. 11, when the frequency area of the addition data $g_n'$ covers the SPR1 (u,v), any addition data $g_n'$ may be used. The scattered component estimation processing unit 288 performs the up-sampling processing and the LPF processing repeatedly on the generated scattered component estimation image of the size of the background data $g_6$ to generate the scattered component estimation image of the same size as the original image data (refer to FIG. 6).

Figure 12:
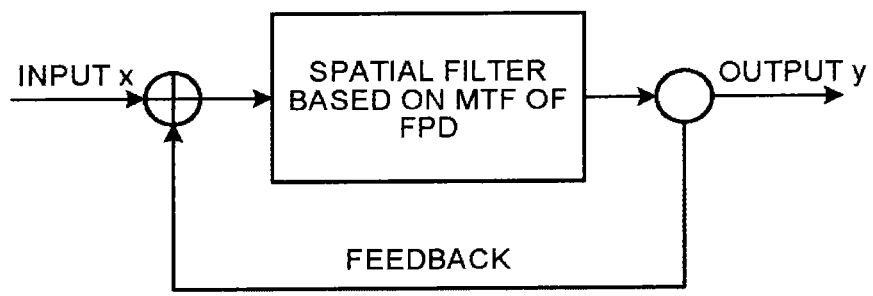
FIG. 12 is a diagram illustrating an example of processing by a resolution correction processing unit according to the first embodiment.

Returning back to FIG. 6, the resolution correction processing unit 289 corrects the resolution that has dropped in accordance with modulation transfer function (MTF) characteristics of the flat panel detector for the image data. Specifically, the resolution correction processing unit 289 corrects the resolution that has dropped by the MTF of the FPD by resolution correction processing by the successive approximation. FIG. 12 is a diagram illustrating an example of the processing by the resolution correction processing unit 289 according to the first embodiment. FIG. 12 illustrates a case of performing the resolution correction processing by the successive approximation of the addition and subtraction type.

As illustrated in FIG. 12, for example, the resolution correction processing unit 289 compares a value obtained by applying a spatial filter determined from the MTF of the FPD 16 by inverse Fourier transformation to an input x with an output y and feeds back a comparison result. The resolution correction processing unit 289 uses noise homogenization reverse processed image data as the output y. In other words, the resolution correction processing unit 289 corrects the resolution to the one before dropping by the MTF of the FPD by the successive approximation that feeds back the difference between the value obtained by applying the spatial filter based on the MTF to the input x and the value of the noise homogenization reverse processed image data and adds it to the input x.

The successive approximation processing by the resolution correction processing unit 289 may be not only the addition and subtraction type but also the multiplication and division type that uses the ratio between the value obtained by applying the spatial filter and the value of the noise homogenization reverse processed image data. By using a ratio to the MTF of a target high-resolution FPD, correction to image data corresponding to the target FPD can also be performed.

Returning back to FIG. 6, the image correcting unit 280 takes the difference between the image data whose resolution has been corrected by the resolution correction processing unit 289 and the scattered component estimation image generated by the scattered component estimation processing unit 288 to produce scattered radiation corrected image data. Thus, the image correcting unit 280 can produce a target image that has been corrected to the scattered radiation of the target grid. By setting the target grid to a grid having higher scattered radiation removal capability than a conventional grid in particular, the contrast decrease by the combination of grid specification/radiation dose/radiation quality of the present embodiment can be sufficiently compensated for. The image correcting unit 280 sends the produced image data to the image processing unit 270. The image processing unit 270 appropriately performs image processing to generate a display image, and the system controller 290 causes the display unit 220 to display the generated display image.

In some examinations, a doctor operates devices such as a guide wire while seeing a fluoroscopic image displayed on a monitor. In this situation, when a time lag between an actual operation and the display of the fluoroscopic image on the monitor is large, accurate operation is hindered. The scattered component estimation processing normally performs Fourier transformation, calculation, and inverse Fourier transformation on the background data $g_6$ and the scattering function reduced to $\frac{1}{64} \times \frac{1}{64}$ for each image collected, in which the delay of the calculation of the scattered component with respect to the timing of the acquisition of the original image is large, and the delay of the fluoroscopic image displayed on the monitor is large. In order to avoid this delay, correction using the scattered component of the previous image may be adopted. In order to prevent flickering in a corrected image caused by fine fluctuations in the scattered component for each image, correction may be performed using an average value of the scattered components of the previous one to a few previous one.

Figure 13:
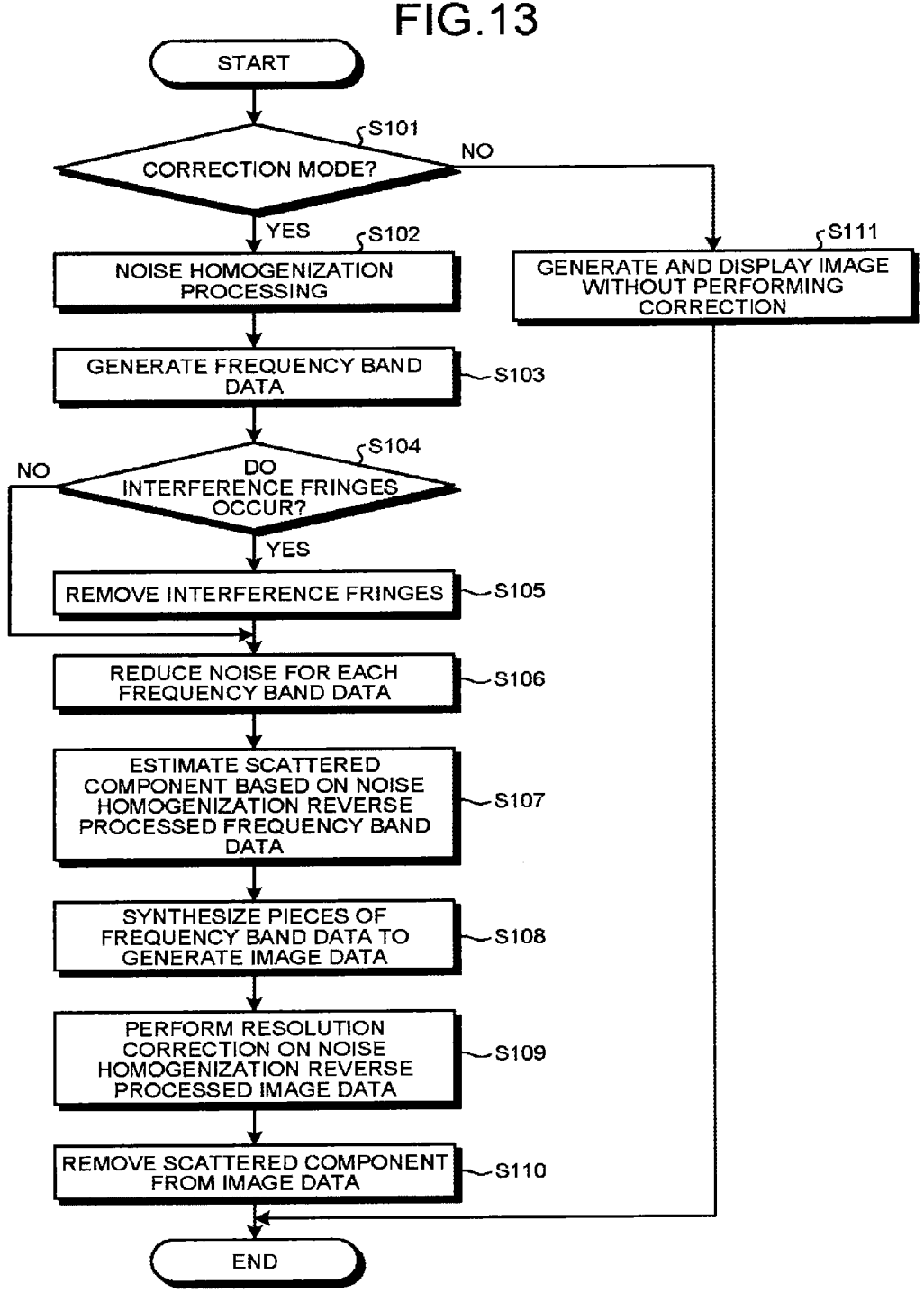
FIG. 13 is a flowchart illustrating a procedure of processing by the X-ray diagnostic apparatus according to the first embodiment.

Next, the processing of the X-ray diagnostic apparatus 1 according to the first embodiment will be described with reference to FIG. 13. FIG. 13 is a flowchart illustrating a procedure of the processing by the X-ray diagnostic apparatus according to the first embodiment. As illustrated in FIG. 13, if the X-ray diagnostic apparatus 1 according to the first embodiment is in a correction mode (Yes at Step S101), the noise homogenization processing unit 282 performs the noise homogenization processing on the original image data (Step S102). The frequency band data generating unit 283 then generates a plurality of pieces of frequency band data from the noise homogenization processed original image data (Step S103).

The interference fringe removal processing unit 284 refers to the image collection mode to determine whether interference fringes occur (Step S104). If it determines that the interference fringes occur (Yes at Step S104), the interference fringe removal processing unit 284 removes the interference fringes by the LPF processing (Step S105), and the noise reduction processing unit 285 reduces the noise for each frequency band data (Step S106). If it determines that interference fringes do not occur at Step S104 (No at Step S104), the interference fringe removal processing is skipped, and the noise reduction processing unit 285 reduces the noise for each frequency band data (Step S106).

Thereafter, the scattered component estimation processing unit 288 estimates the scattered component based on the noise homogenization reverse processed frequency band data (the background data) (Step S107). The frequency band data synthesizing unit 286 synthesizes the pieces of noise-reduced frequency band data to generate the image data of the same size as the original image data (Step S108). The resolution correction processing unit 289 performs the resolution correction processing on the noise homogenization reverse processed image data (Step S109).

The image correcting unit 280 takes the difference between the resolution-corrected image data and the scattered component estimation image to remove the scattered component from the image data (Step S110) and ends the processing. Incidentally, if not being the correction mode at Step S101, the X-ray diagnostic apparatus 1 generates and displays an image without performing correction (Step S111).

As described above, in the first embodiment, the X-ray generator (the X-ray tube 12) generates X-rays. The FPD 16 detects the X-rays. The grid 15 has a lattice density so that the frequency of the interference fringes caused by the interference with the pixels of the FPD 16 is within a range of the Nyquist frequency of the FPD to half the Nyquist frequency. The frequency band data generating unit (also called the converting unit) 283 converts the original image data based on the X-rays having passed through the grid 15 and detected by the FPD 16 into a plurality of pieces of frequency band data and the background data. The interference fringe removal processing unit 284 removes interference fringes contained in at least one piece of frequency band data among the pieces of frequency band data. The noise reduction processing unit 285 reduces the noise contained in the frequency band data. The scattered component estimation processing unit 288 corrects the scattered radiation component contained in the background data or the data under generation after being processed by the respective processing units based on the difference between the scattered radiation component contained in the X-rays having passed through the grid 15 and the scattered radiation component contained in the X-rays having passed through the target grid having higher scattered radiation removal capability than the grid 15. The frequency band data synthesizing unit 286 synthesizes the pieces of frequency band data after being processed by the respective processing units to generate the image data. The resolution correction processing unit 289 corrects the resolution that has dropped in accordance with the MTF characteristics of the FPD for the image data. The image correcting unit 280 generates the scattered radiation component estimated by the scattered component estimation processing unit 288 in the size of the original image data and takes the difference between it and the resolution-corrected image data to correct the scattered radiation. Thus, the X-ray diagnostic apparatus 1 according to the first embodiment can increase the degree of freedom of the combination of grid specification/radiation dose/radiation quality and can reduce the exposure dose while maintaining image quality.

The X-ray diagnostic apparatus 1, for example, can remarkably improve a balance between a radiation dose and an image by the above configuration. The X-ray diagnostic apparatus 1, for example, can reduce the exposure dose to 60% or less if the image quality is the same level as conventional image quality. The X-ray diagnostic apparatus 1, for example, can remarkably improve image quality if the exposure dose is the same level as conventional one. The X-ray diagnostic apparatus 1, for example, can produce an image without interference fringes caused by the pixels of the FPD and the lattice of the grid and without a noise increase and a contrast decrease. From these facts, the X-ray diagnostic apparatus 1 can reduce the exposure dose without deteriorating the performance of diagnosing X-ray images.

In the first embodiment, the grid 15 has a lattice density so that the frequency of the interference fringes is a frequency, within a range of the Nyquist frequency of the FPD 16 to half the Nyquist frequency, nearer to the Nyquist frequency. Thus, the X-ray diagnostic apparatus 1 according to the first embodiment can remove components corresponding to the interference fringes without removing the signal components.

In the first embodiment, the grid 15 is formed with a lattice ratio and of an intermediate substance that cause the direct radiation contained in the X-rays having passed through the subject to pass therethrough easily. Thus, the X-ray diagnostic apparatus 1 according to the first embodiment can inhibit a decrease in the signal component and can maintain image quality.

In the first embodiment, the grid 15 has the lattice ratio represented as a ratio of foil interval to thickness, within a range of 1:6 to 1:10 and has fiber as the intermediate substance. Thus, the X-ray diagnostic apparatus 1 according to the first embodiment can improve the transmittance of the direct radiation.

In the first embodiment, the noise reduction processing unit 285 reduces the noise contained in a plurality of pieces of frequency band data, the noise being homogenized so as to be constant regardless of the pixel value. Thus, the X-ray diagnostic apparatus 1 according to the first embodiment can improve the noise reduction effect.

Second Embodiment

Although the first embodiment has been described, various different forms other than the first embodiment may be embodied.

Figure 14:
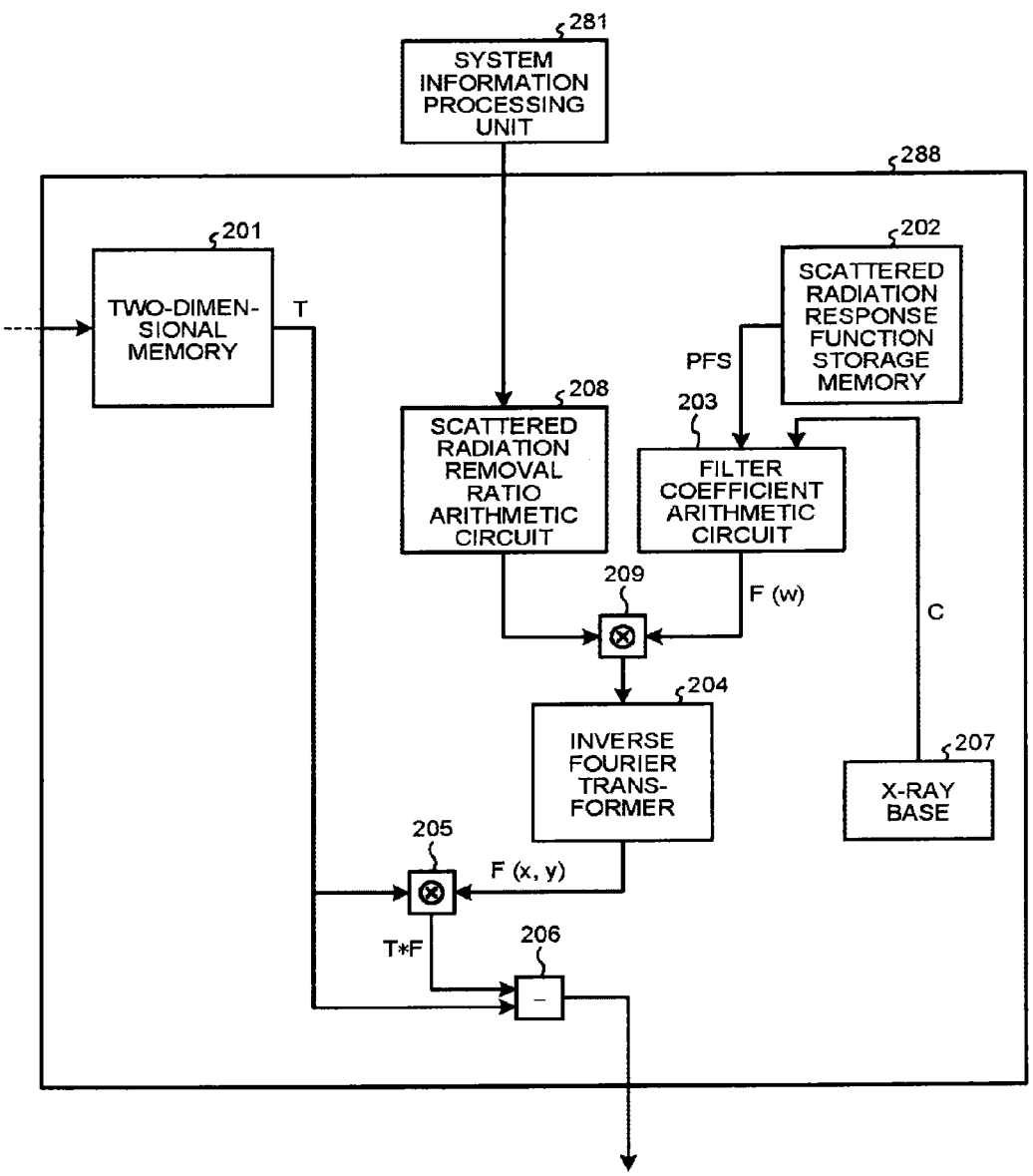
FIG. 14 is a diagram for illustrating processing by a scattered component estimation processing unit according to a second embodiment.

The scattered component estimation processing described in the first embodiment with reference to FIG. 10 may be performed not only by the above example but also other methods. FIG. 14 is a diagram for illustrating processing by the scattered component estimation processing unit 288 according to a second embodiment. The scattered component estimation processing unit 288, for example, can be implemented by the circuit illustrated in FIG. 14. The circuit is a modification of FIG. 1 disclosed in Japanese Patent No. 2509181. A two-dimensional memory 201, a scattered radiation response function storage memory 202, a filter coefficient arithmetic circuit 203, an inverse Fourier transformer 204, a filter arithmetic circuit 205, a subtracter 206, and an X-ray base 207 correspond to the two-dimensional memory 1, the scattered radiation response function storage memory 2, the filter coefficient arithmetic circuit 3, the inverse Fourier transformer 4, the filter arithmetic circuit 5, the subtracter 6, and the X-ray base 7 in FIG. 1 of the document. The second embodiment further includes a scattered radiation removal ratio arithmetic circuit 208 and a multiplier 209.

The scattered radiation removal ratio arithmetic circuit 208 receives conditions such as the tube voltage, the irradiation field area, and the subject thickness from the system information processing unit 281 and calculates a scattered radiation removal ratio corresponding to the conditions. The scattered radiation removal ratio is a coefficient representing what amount of a scattered radiation dose when using the grid 15 should be deleted to achieve correction to the scattered radiation dose of the target grid. The scattered radiation removal ratio varies by conditions such as the tube voltage, the irradiation field area, and the subject thickness. A calculating equation may be set in advance based on experimental results or the like. Alternatively, the scattered radiation removal ratio may be experimentally determined for each condition such as the tube voltage, the irradiation field area, and the subject thickness in advance, the result may be stored in a memory or the like of the scattered radiation removal ratio arithmetic circuit 208, and the scattered radiation removal ratio arithmetic circuit 208 may select the scattered radiation removal ratio out of the memory.

The multiplier 209 multiplies the filter coefficient calculated by the filter coefficient arithmetic circuit 203 by the scattered radiation removal ratio calculated by the scattered radiation removal ratio arithmetic circuit 208 to correct the filter coefficient. The inverse Fourier transformer 204, the filter arithmetic circuit 205, and the subtracter 206 perform the processing using the filter coefficient after being thus corrected.

Even when using the above circuit, the difference between the background data (or the frequency band data) actually collected and the X-ray image data obtained when using the target grid whose scattered radiation dose is not zero can be calculated.

Although the first embodiment describes a case of performing the LPF processing as the interference fringe removal processing, embodiments are not so limited, and the interference fringe removal processing may be performed by processing using wavelet conversion disclosed in Japanese Patent Application Laid-open No. 2011-10829.

Although the first embodiment describes a case of generating the low-resolution data by performing the down-sampling processing, embodiments are not so limited, and the entire processing may be performed with the same size as the original image data. In such a case, for example, the down-sampling processing, the up-sampling processing, and the LPF processing after the up-sampling processing by the frequency band data generating unit 283 illustrated in FIG. 6 are omitted. In such a case, for example, the up-sampling processing and the LPF processing after the up-sampling processing by the frequency band data synthesizing unit 286, the up-sampling processing after the scattered component estimation processing, and the LPF processing after the up-sampling processing illustrated in FIG. 6 are omitted.

The configuration of the X-ray diagnostic apparatus 1 according to the embodiment is merely an example, and integration and separation of the respective units can be appropriately performed. The configuration illustrated in FIG. 6 is, for example, merely an example and can be appropriately changed.

Although the first and the second embodiments describe a case of performing various processing by the X-ray diagnostic apparatus that performs examination and treatment on alimentary canals, the urinary organs, orthopedics, interventional radiology (IVR), or the like, embodiments are not so limited, and an X-ray angiographic apparatus that performs examination and treatment on brains and the circulatory system including hearts, for example, may perform the various processing.

Although the first and the second embodiments describe a case in which the X-ray diagnostic apparatus performs the various processing, embodiments are not so limited, and a medical image processing apparatus such as a workstation, for example, may perform the various processing. In such a case, for example, the workstation having the image correcting unit 280 performs the various processing on the original image data collected by the X-ray diagnostic apparatus having the grid 15.

Although the first and the second embodiments describe a case of performing the processing on the original image data collected by the X-ray diagnostic apparatus having the grid 15, embodiments are not so limited, and the processing, for example, may be performed on the original image data collected by an X-ray diagnostic apparatus (a gridless X-ray diagnostic apparatus) without the grid 15. Even the gridless X-ray diagnostic apparatus, for example, can also reduce radiation exposure while maintaining image quality by performing the above pieces of processing.

Being gridless does not produce any interference fringes caused by the pixels of the FPD and the lattice of the grid. Accordingly, the gridless X-ray diagnostic apparatus performs the various pieces of correction processing (the noise reduction processing and the scattered component and resolution correction processing) without performing the interference fringe removal processing. The gridless X-ray diagnostic apparatus, for example, includes the image correcting unit 280 (refer to FIG. 6) without the interference fringe removal processing unit 284 and performs the various pieces of correction processing on the original image data generated by the image data generating unit 250 under the control of the system controller 290.

In the gridless X-ray diagnostic apparatus, for example, the noise homogenization processing unit 282 accepts the original image data without interference fringes from the image data generating unit 250 and performs the noise homogenization processing on the accepted original image data. The frequency band data generating unit 283 converts the original image data into a plurality of pieces of frequency band data. The frequency band data generating unit 283, for example, generates the pieces of frequency band data containing respective certain frequency bands and a piece of background data from the original image data whose noise has been homogenized by the noise homogenization processing unit 282.

In the gridless X-ray diagnostic apparatus, without performing the interference fringe removal processing on the pieces of frequency band data generated by the frequency band data generating unit 283, all pieces of frequency band data are sent from the frequency band data generating unit 283 to the noise reduction processing unit 285. The noise reduction processing unit 285 reduces the noise contained in the frequency band data. Specifically, the noise reduction processing unit 285 reduces the noise contained the respective pieces of frequency band data accepted from the frequency band data generating unit 283.

The frequency band data synthesizing unit 286 synthesizes the pieces of frequency band data to generate image data. Specifically, the frequency band data synthesizing unit 286 successively synthesizes the background data and the noise-reduced frequency band data to generate noise-reduced image data of the same size as the original image data. The noise homogenization reverse processing unit 287 performs the noise homogenization reverse processing on the generated image data. The resolution correction processing unit 289 corrects the resolution that has dropped by the MTF of the FPD by the resolution correction processing by the successive approximation and the resolution of the noise homogenization reverse processed image data.

The scattered component estimation processing unit 288 of the gridless X-ray diagnostic apparatus corrects the scattered radiation component of the original image data based on the scattered radiation component contained in the X-rays detected by the FPD 16 and the scatted radiation component contained in the X-rays having passed through a grid having a certain scattered radiation removal capability. In other words, the scattered component estimation processing unit 288 estimates the difference between the scattered radiation component contained in the X-rays not having passed through the grid and detected by the FPD 16 and the scattered radiation component contained in the X-rays having passed through the grid (the target grid having higher scattered radiation removal capability than the grid 15, for example) having the certain scattered radiation removal capability and corrects the scattered radiation component based on the estimated difference. The X-rays detected by the FPD 16 of the gridless X-ray diagnostic apparatus contain more scattered radiation than the X-rays having passed through the grid 15.

The scattered component estimation processing unit 288 of the gridless X-ray diagnostic apparatus generates, for example, a scattered radiation image for correcting such much scattered radiation as if removed by the target grid by a converted image and a scattering function. Specifically, the scattered component estimation processing unit 288 generates the scattered radiation image using noise homogenization reverse processed background data or the converted image converted from the addition data, a scattering function when using no grid, and the scattering function of the grid (the target grid having higher scattered radiation removal capability than the grid 15, for example) having the certain scattered radiation removal capability.

The image correcting unit 280 takes the difference between the image data whose resolution has been corrected by the resolution correction processing unit 289 and the scattered component estimation image generated by the scattered component estimation processing unit 288 to generate scattered radiation corrected image data.

Although the embodiment describes a case in which the gridless X-ray diagnostic apparatus performs the various processing, embodiments are not so limited, and a medical image processing apparatus such as a workstation, for example, may perform the various processing. In such a case, for example, the workstation having the image correcting unit 280 without the interference fringe removal processing unit 284 performs the various processing on the original image data collected by the gridless X-ray diagnostic apparatus.

(Another Embodiment)

Figure 15:
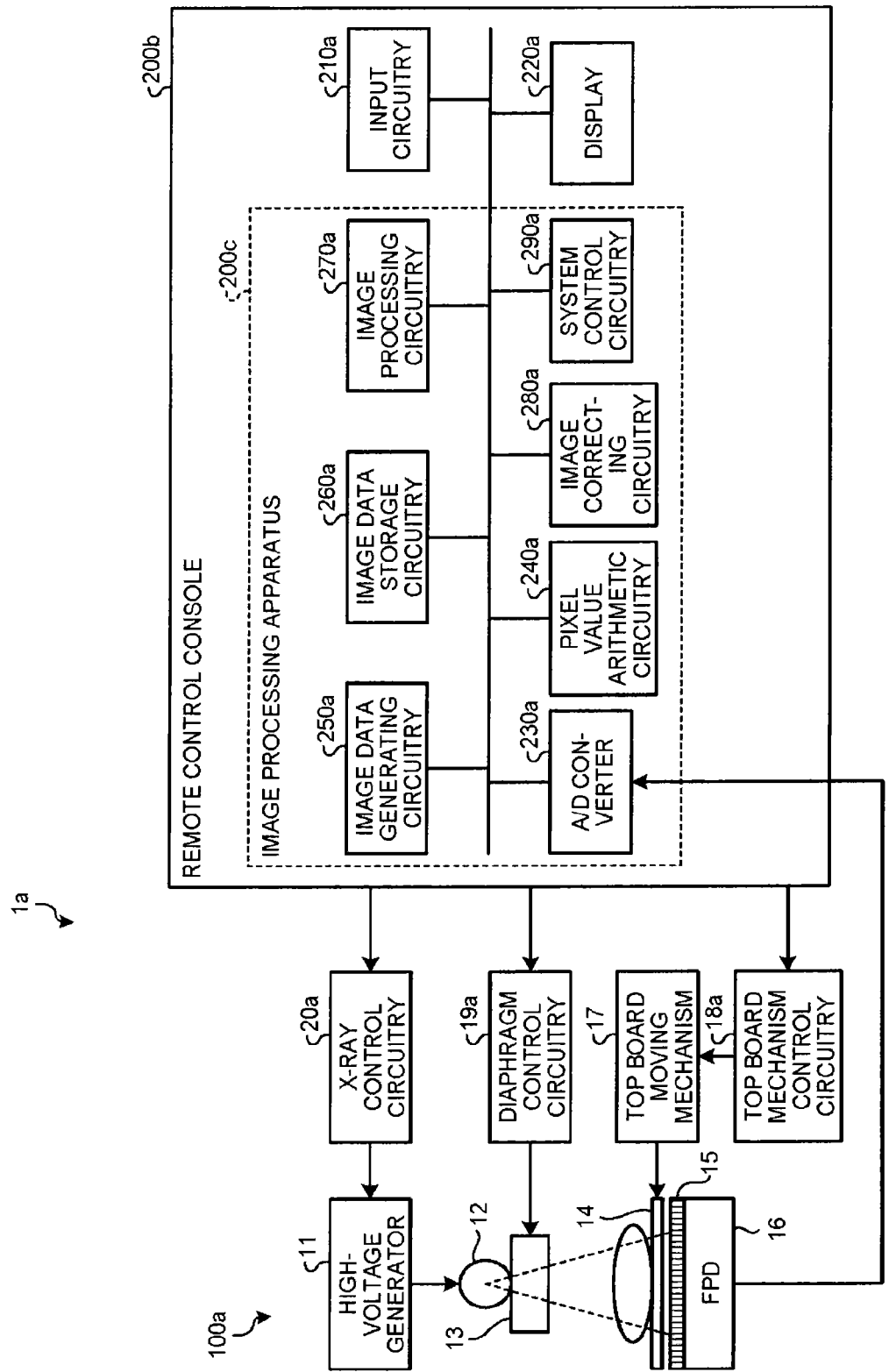
FIG. 15 is a diagram illustrating an example of the configuration of an X-ray image diagnostic apparatus according to another embodiment.
Figure 16:
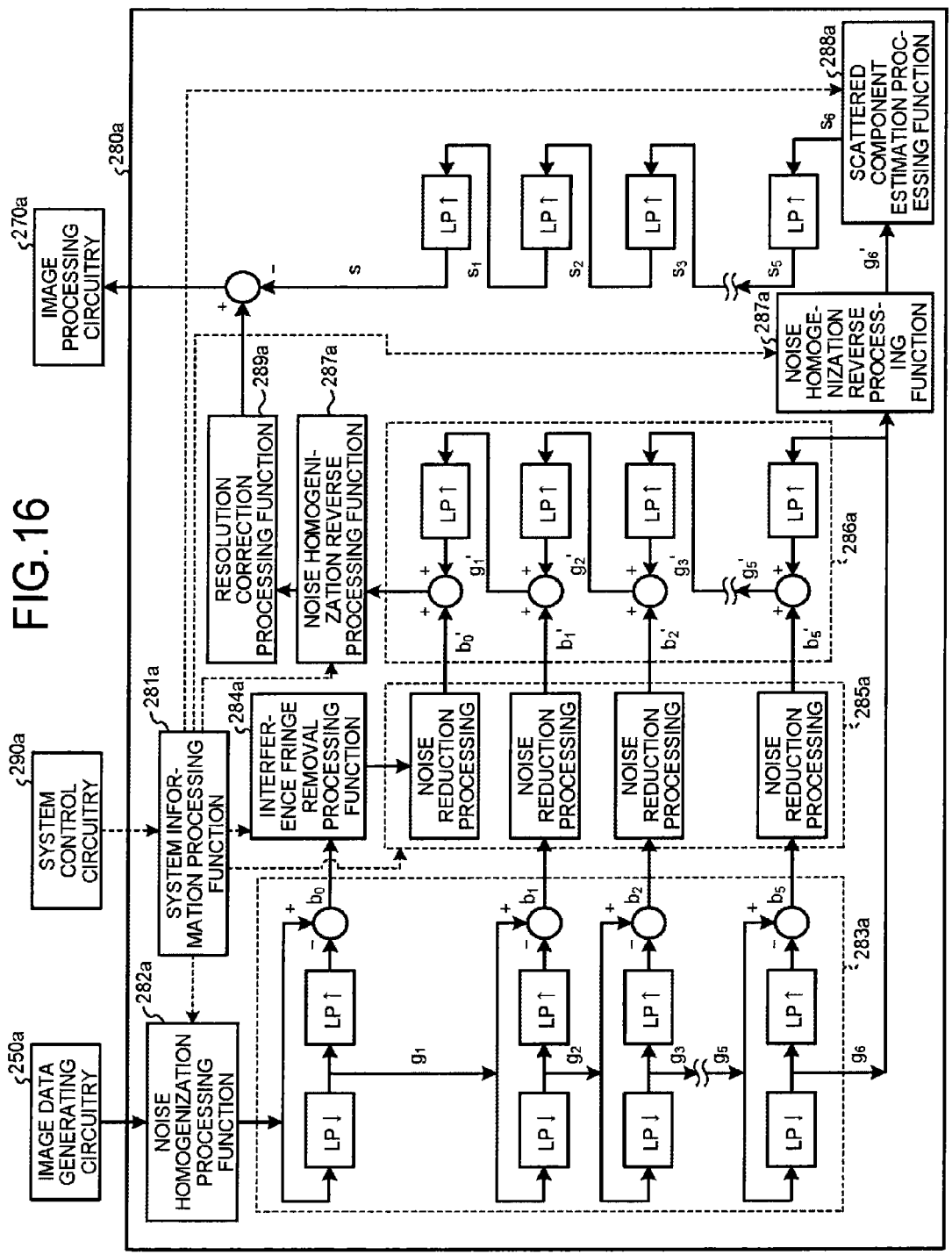
FIG. 16 is a diagram illustrating an example of the configuration of an image correcting unit according to another embodiment.

Another embodiment of the X-ray image diagnostic apparatus described above will be described with reference to FIG. 15 and FIG. 16. FIG. 15 is a diagram illustrating an example of the configuration of an X-ray image diagnostic apparatus according to another embodiment. FIG. 16 is a diagram illustrating an example of the configuration of an image correcting unit according to another embodiment. In another embodiment, the points different from the above embodiments are mainly explained, and as for functions similar to the components explained in the above embodiment, the same reference numerals are given thereto, and explanation thereof is omitted. As illustrated in FIG. 15, the X-ray image diagnostic apparatus 1a according to another embodiment includes an apparatus main body 100a and a remote control console 200b. As illustrated in FIG. 15, the apparatus main body 100a includes the high-voltage generator 11, the X-ray tube 12, the X-ray movable diaphragm 13, the top board 14, the grid 15, the flat panel detector (FPD) 16, the top board moving mechanism 17, a top board mechanism control circuitry 18a, a diaphragm control circuitry 19a, and an X-ray control circuitry 20a and is placed in the examination room. As illustrated in FIG. 15, the remote control console 200b includes an image processing apparatus 200c, an input circuitry 210a, and a display 220a and is placed in the operation room, for example. As illustrated in FIG. 15, the image processing apparatus 200c includes an A/D converter 230a, a pixel value arithmetic circuitry 240a, an image data generating circuitry 250a, an image data storage circuitry 260a, an image processing circuitry 270a, an image correcting circuitry 280a, and the system control circuitry 290a. As illustrated in FIG. 15, each circuitry is connected in each other and to transmit and receive various signals to each other.

The top board mechanism control circuitry 18a corresponds to the top board mechanism controller 18 illustrated in FIG. 2. The diaphragm control circuitry 19a corresponds to the diaphragm controller 19 illustrated in FIG. 2. The X-ray control circuitry 20a corresponds to the X-ray controller 20 illustrated in FIG. 2. The input circuitry 210a corresponds to the input unit 210 illustrated in FIG. 2. The display 220a corresponds to the display unit 220 illustrated in FIG. 2. The A/D converter 230a corresponds to the A/D converting unit 230 illustrated in FIG. 2. The pixel value arithmetic circuitry 240a corresponds to the pixel value arithmetic unit 240 illustrated in FIG. 2. The image data generating circuitry 250a corresponds to the image data generating unit 250 illustrated in FIG. 2. The image data storage circuitry 260a corresponds to the image data storage unit 260 illustrated in FIG. 2. The image processing circuitry 270a corresponds to the image processing unit 270 illustrated in FIG. 2. The image correcting circuitry 280a corresponds to the image correcting unit 280 illustrated in FIG. 2. The system control circuitry 290a corresponds to trie system controller 290 illustrated in FIG. 2.

In the present embodiment, the respective processing functions performed by the top board mechanism control circuitry 18a, the diaphragm control circuitry 19a, the X-ray control circuitry 20a, the pixel value arithmetic circuitry 240a, the image data generating circuitry 250a, the image processing circuitry 270a, the image correcting circuitry 280a, and the system control circuitry 290a illustrated in FIG. 15 or FIG. 16 are stored in the image data storage circuitry 260a, in the form of a computer-executable program.

Each of the top board mechanism control circuitry 18a, the diaphragm control circuitry 19a, the X-ray control circuitry 20a, the pixel value arithmetic circuitry 240a, the image data generating circuitry 250a, the image processing circuitry 270a, the image correcting circuitry 280a, and the system control circuitry 290a is a processor that loads programs from the image data storage circuitry 260a, and executes the programs so as to implement the respective functions corresponding to the programs. In other words, each circuitry that has loaded the programs has the functions corresponding to the programs loaded. The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions.

The image data storage circuitry 260a, for example, stores therein computer programs corresponding to a system information processing function 281a, a noise homogenization processing function 282a, a frequency band data generating function 283a, an interference fringe removal processing function 284a, a noise reduction processing function 285a, a frequency band data synthesizing function 286a, a noise homogenization reverse processing function 287a, a scattered component estimation processing function 288a, and a resolution correction processing function 289a illustrated in FIG. 16. The image correcting circuitry 280a reads the program corresponding to the system information processing function 281a from the image data storage circuitry 260a and executes the program, thereby performing processing similar to the system information processing unit 281. The image correcting circuitry 280a reads the program corresponding to the noise homogenization processing function 282a from the image data storage circuitry 260a and executes the program, thereby performing processing similar to the noise homogenization processing unit 282. The image correcting circuitry 280a reads the program corresponding to the frequency band data generating function 283a from the image data storage circuitry 260a and executes the program, thereby performing processing similar to the frequency band data generating unit 283. The image correcting circuitry 280a reads the program corresponding to the interference fringe removal processing function 284a from the image data storage circuitry 260a and executes the program, thereby performing processing similar to the interference fringe removal processing unit 284.

The image correcting circuitry 280a reads the program corresponding to the noise reduction processing function 285a from the image data storage circuitry 260a and executes the program, thereby performing processing similar to the noise reduction processing unit 285.

The image correcting circuitry 280a reads the program corresponding to the frequency band data synthesizing function 286a from the image data storage circuitry 260a and executes the program, thereby performing processing similar to the frequency band data synthesizing unit 286. The image correcting circuitry 280a reads the program corresponding to the noise homogenization reverse processing function 287a from the image data storage circuitry 260a and executes the program, thereby performing processing similar to the noise homogenization reverse processing unit 287. The image correcting circuitry 280a reads the program corresponding to the scattered component estimation processing function 288a from the image data storage circuitry 260a and executes the program, thereby performing processing similar to the scattered component estimation processing unit 288. The image correcting circuitry 280a reads the program corresponding to the resolution correction processing function 289a from the image data storage circuitry 260a and executes the program, thereby performing processing similar to the resolution correction processing unit 289.

The image data storage circuitry 260a, for example, stores therein computer programs corresponding to a top board mechanism control function, a diaphragm control function, a X-ray control function, a pixel value arithmetic function, an image data generating function, an image processing function, and a system control function. Each of the top board mechanism control circuitry 18a, the diaphragm control circuitry 19a, the X-ray control circuitry 20a, the pixel value arithmetic circuitry 240a, the image data generating circuitry 250a, the image processing circuitry 270a, and the system control circuitry 290a reads the program corresponding to the top board mechanism control function, the diaphragm control function, the X-ray control function, the pixel value arithmetic function, the image data generating function, the image processing function, and the system control function from the image data storage circuitry 260a and executes the program respectively, thereby performing processing similar to the top board mechanism controller 18, the diaphragm controller 19, the X-ray controller 20, the pixel value arithmetic unit 240, the image data generating unit 250, the image processing unit 270, and the system control unit 290.

The example illustrated in FIG. 16 describes a case of implementing the system information processing function 281a, the noise homogenization processing function 282a, the frequency band data generating function 283a, the interference fringe removal processing function 284a, the noise reduction processing function 285a, the frequency band data synthesizing function 286a, the noise homogenization reverse processing function 287a, the scattered component estimation processing function 288a, and the resolution correction processing function 289a by causing one image correcting circuitry 280a to execute the respective programs. However, embodiments are not so limited, and for example, a plurality of processing circuits may implement system information processing function 281a, the noise homogenization processing function 282a, the frequency band data generating function 283a, the interference fringe removal processing function 284a, the noise reduction processing function 285a, the frequency band data synthesizing function 286a, the noise homogenization reverse processing function 287a, the scattered component estimation processing function 288a, and the resolution correction processing function 289a. For example, one or more functions among the system information processing function 281a, the noise homogenization processing function 282a, the frequency band data generating function 283a, the interference fringe removal processing function 284a, the noise reduction processing function 285a, the frequency band data synthesizing function 286a, the noise homogenization reverse processing function 287a, the scattered component estimation processing function 288a, and the resolution correction processing function 289a may be separately implemented in exclusive, independent program execution circuits.

Some of the circuitry illustrated in FIG. 15 and FIG. 16 may be implemented as one processing circuit. For example, one program execution circuit may implement the top board mechanism control function implemented by the top board mechanism control circuitry 18a, the diaphragm control function implemented by t the diaphragm control circuitry 19a, the X-ray control function implemented by the X-ray control circuitry 20a, the pixel value arithmetic function implemented by the pixel value arithmetic circuitry 240a, the image data generating function implemented by the image data generating circuitry 250a, the image processing function implemented by the image processing circuitry 270a, the system control function implemented by the system control circuitry 290a, and the system information processing function 281a, the noise homogenization processing function 282a, the frequency band data generating function 283a, the interference fringe removal processing function 284a, the noise reduction processing function 285a, the frequency band data synthesizing function 286a, the noise homogenization reverse processing function 287a, the scattered component estimation processing function 288a, and the resolution correction processing function 289a implemented by the image correcting circuitry 280a.

The input circuitry 115a is implemented by a trackball, a switch button, a mouse, a keyboard, or the like for performing the setting of a ROI (region of interest) or the like. The input circuitry 115a is connected to the system control circuitry 21a, converts input operation received from an operator into an electric signal, and outputs the electric signal to the system control circuitry 21a or the processing circuitry 200.

S Step S102 in FIG. 13 is a step implemented by causing the image correcting circuitry 280a to read the program corresponding to the noise homogenization processing function 282a from the image data storage circuitry 260a and to execute the program. Step S103 in FIG. 13 is a step implemented by causing the image correcting circuitry 280a to read the program corresponding to the frequency band data generating function 283a from the image data storage circuitry 260a and to execute the program. Step S104 and step S105 in FIG. 13 is a step implemented by causing the image correcting circuitry 280a to read the program corresponding to the interference fringe removal processing function 284a from the image data storage circuitry 260a and to execute the program. Step S106 in FIG. 13 is a step implemented by causing the image correcting circuitry 280a to read the program corresponding to the noise reduction processing function 285a from the image data storage circuitry 260a and to execute the program. Step S107 in FIG. 13 is a step implemented by causing the image correcting circuitry 280a to read the program corresponding to the scattered component estimation processing function 288a from the image data storage circuitry 260a and to execute the program. Step S108 in FIG. 13 is a step implemented by causing the image correcting circuitry 280a to read the program corresponding to the frequency band data synthesizing function 286a from the image data storage circuitry 260a and to execute the program. Step S109 in FIG. 13 is a step implemented by causing the image correcting circuitry 280a to read the program corresponding to the resolution correction processing function 289a from the image data storage circuitry 260a and to execute the program.

As described above, the X-ray diagnostic apparatus and the image processing apparatus according to the first and the second embodiments can reduce radiation exposure while maintaining image quality.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
an X-ray generator configured to generate X-rays;
a flat panel detector configured to detect the X-rays;
a grid provided between the X-ray generator and the flat panel detector; and
processing circuitry configured to
perform noise homogenization processing on original image data, obtained based on X-rays having passed through the grid and detected by the flat panel detector, to generate processed original image data in which pixel-value dependence of noise is reduced,
convert the processed original image data into a plurality of pieces of frequency band data,
remove interference fringes contained in at least one piece of frequency band data among the pieces of frequency band data,
reduce noise contained in the pieces of frequency band data,
generate image data by adding a plurality of pieces of the noise-reduced frequency band data,
perform noise homogenization reverse processing on the generated image data to generate processed image data, and
correct a scattered radiation component of the processed image data based on a difference between a scattered radiation component contained in the X-rays having passed through the grid and a scattered radiation component that results when the X-rays pass through a virtual grid that removes scattered radiation to a larger extent than the grid, wherein the virtual grid is not present when obtaining the original image data.

2. The X-ray diagnostic apparatus according to claim 1, wherein the grid has a lattice density so that a frequency of the interference fringes is a frequency, within a range of a Nyquist frequency of the flat panel detector to half the Nyquist frequency, nearer to the Nyquist frequency.

3. The X-ray diagnostic apparatus according to claim 1, wherein the grid is formed with a lattice ratio and of an intermediate substance that cause direct radiation contained in X-rays having passed through a subject to pass therethrough easily.

4. The X-ray diagnostic apparatus according to claim 2, wherein the grid is formed with a lattice ratio and of an intermediate substance that cause direct radiation contained in X-rays having passed through a subject to pass therethrough easily.

5. The X-ray diagnostic apparatus according to claim 3, wherein the grid has the lattice ratio represented as a ratio of foil interval to thickness, within a range of 1:6 to 1:10 and has fiber as an intermediate substance.

6. The X-ray diagnostic apparatus according to claim 4, wherein the grid has the lattice ratio represented as a ratio of foil interval to thickness, within a range of 1:6 to 1:10 and has fiber as an intermediate substance.

7. The X-ray diagnostic apparatus according to claim 1, wherein the processing circuitry is configured to reduce the noise contained in the pieces of frequency band data, the noise being homogenized so as to be constant regardless of a pixel value.

8. The X-ray diagnostic apparatus according to claim 2, wherein the processing circuitry is configured reduce the noise contained in the pieces of frequency band data, the noise being homogenized so as to be constant regardless of a pixel value.

9. The X-ray diagnostic apparatus according to claim 3, wherein the processing circuitry is configured to reduce the noise contained in the pieces of frequency band data, the noise being homogenized so as to be constant regardless of a pixel value.

10. The X-ray diagnostic apparatus according to claim 4, wherein the processing circuitry is configured to reduce the noise contained in the pieces of frequency band data, the noise being homogenized so as to be constant regardless of a pixel value.

11. The X-ray diagnostic apparatus according to claim 5, wherein the processing circuitry is configured to reduce the noise contained in the pieces of frequency band data, the noise being homogenized so as to be constant regardless of a pixel value.

12. The X-ray diagnostic apparatus according to claim 6, wherein the processing circuitry is configured to reduce the noise contained in the pieces of frequency band data, the noise being homogenized so as to be constant regardless of a pixel value.

13. An image processing apparatus, comprising:
processing circuitry configured to
  perform noise homogenization processing on original image data, obtained based on X-rays having passed through a grid and detected by a flat panel detector, to generate processed original image data in which pixel-value dependence of noise is reduced,
  convert the processed original image data into a plurality of pieces of frequency band data,
  remove interference fringes contained in at least one piece of frequency band data among the pieces of frequency band data,
  reduce noise contained in the pieces of frequency band data,
  generate image data by adding a plurality of pieces of the noise-reduced frequency band data,
  perform noise homogenization reverse processing on the generated image data to generate processed image data, and
  correct a scattered radiation component of the processed image data based on a difference between a scattered radiation component contained in the X-rays having passed through the grid and a scattered radiation component that results when the X-rays pass through a virtual grid that removes scattered radiation to a larger extent than the grid, wherein the virtual grid is not present when obtaining the original image data.

14. The image processing apparatus according to claim 13, wherein the processing circuitry is configured to reduce the noise contained in the pieces of frequency band data, the noise being homogenized so as to be constant regardless of a pixel value.

15. An image processing apparatus, comprising:
processing circuitry configured to
  perform noise homogenization processing on original image data, obtained based on X-rays having passed through a grid and detected by a flat panel detector, to generate processed original image data in which pixel-value dependence of noise is reduced,
  convert the processed original image data into a plurality of pieces of frequency band data,
  reduce noise contained in the pieces of frequency band data,
  generate image data by adding a plurality of pieces of the noise-reduced frequency band data,
  perform noise homogenization reverse processing on the generated image data to generate processed image data, and
  correct a scattered radiation component of the processed image data based on a difference between a scattered radiation component contained in the X-rays detected by the flat panel detector and a scattered radiation component that results when the X-rays pass through a virtual grid that removes scattered radiation to a larger extent than the grid, wherein the virtual grid is not present when obtaining the original image data.

16. The image processing apparatus according to claim 15, wherein the processing circuitry is configured to reduce the noise contained in the pieces of frequency band data, the noise being homogenized so as to be constant regardless of a pixel value.

17. An X-ray diagnostic apparatus, comprising:
an X-ray generator configured to generate X-rays;
a flat panel detector configured to detect the X-rays;
a grid provided between the X-ray generator and the flat panel detector: and
processing circuitry configured to
  convert original image data based on X-rays having passed through the grid and detected by the flat panel detector into a plurality of pieces of frequency band data,
  remove interference fringes contained in at least one piece of frequency band data among the pieces of frequency band data,
  reduce noise contained in the pieces of frequency band data,
  correct a scattered radiation component of the original image data, based on a difference between a scattered radiation component contained in the X-rays having passed through the grid and a scattered radiation component that results when the X-rays pass through a virtual grid that removes scattered radiation to a larger extent than the grid, wherein the virtual grid is not present when obtaining the original image data, and
  generate image data by adding a plurality of pieces of frequency band data after being processed.

18. An image processing apparatus, comprising:

processing circuitry configured to convert original image data based on X-rays having passed through a grid and detected by a flat panel detector into a plurality of pieces of frequency band data, remove interference fringes contained in at least one piece of frequency band data among the pieces of frequency band data, reduce noise contained the pieces of frequency band data, correct a scattered radiation component of the original image data based on a difference between a scattered radiation component contained in the X-rays having passed through the grid and a scattered radiation component that results when the X-rays pass through a virtual grid that removes scattered radiation to a larger extent than the grid, wherein the virtual grid is not present when obtaining the original image data, and generate image data by adding a plurality of pieces of frequency band data after being processed.

19. An image processing apparatus, comprising:

processing circuitry configured to convert processed original image data based on X-rays having passed through a grid and detected by a flat panel detector into a plurality of pieces of frequency band data, reduce noise contained in the pieces of frequency band data, correct a scattered radiation component of the original image data based on a difference between a scattered radiation component contained in the X-rays having passed through the grid and a scattered radiation component that results when the X-rays pass through a virtual grid that removes scattered radiation to a larger extent than the grid, wherein the virtual grid is not present when obtaining the original image data, and generate image data by adding a plurality of pieces of frequency band data after being processed.

* * * * *